United States Patent [19]

Vanlerberghe et al.

[11] 4,189,468
[45] Feb. 19, 1980

[54] CROSSLINKED POLYAMINO-POLYAMIDE IN HAIR CONDITIONING COMPOSITIONS

[75] Inventors: Guy Vanlerberghe, Claye-Souilly; Henri Sebag, Paris; Jean-Francois Grollier, Paris; Alexandre Zysman, Paris, all of France

[73] Assignee: L'Oreal, Paris, France

[21] Appl. No.: 881,513

[22] Filed: Feb. 27, 1978

Related U.S. Application Data

[63] Continuation-in-part of Ser. No. 762,804, Jan. 26, 1977, which is a continuation of Ser. No. 528,577, Nov. 29, 1974, abandoned.

[30] Foreign Application Priority Data

Nov. 30, 1973 [LU] Luxembourg .............. 68901
Mar. 2, 1977 [FR] France .............. 77 06031

[51] Int. Cl.$^2$ .............................. A61K 7/06
[52] U.S. Cl. .......................... 424/70; 260/29.2 N; 424/DIG. 1; 424/DIG. 2; 424/47; 424/71; 544/357; 544/374; 544/387; 525/423; 525/426; 525/419; 525/435
[58] Field of Search ............... 424/DIG. 1, DIG. 2, 424/47, 70, 71; 260/785 C, 29.2 N; 528/333, 334

[56] References Cited

U.S. PATENT DOCUMENTS

| | | | |
|---|---|---|---|
| 2,882,185 | 4/1959 | Valko et al. | 260/78 SC |
| 2,926,116 | 2/1960 | Keim | 260/78 SC |
| 2,926,154 | 2/1960 | Keim | 260/78 SC |
| 3,560,609 | 2/1971 | Korden | 424/71 X |
| 3,560,610 | 2/1971 | Korden | 424/71 X |

FOREIGN PATENT DOCUMENTS

| | | |
|---|---|---|
| 2617528 | 12/1976 | Fed. Rep. of Germany. |
| 1583363 | 9/1969 | France. |
| 2249104 | 5/1975 | France. |

*Primary Examiner*—Bernard Helfin
*Assistant Examiner*—Vera C. Clarke
*Attorney, Agent, or Firm*—Cushman, Darby & Cushman

[57] ABSTRACT

A cosmetic composition for the hair comprises at least one water-soluble crosslinked polymer obtained by crosslinking a polyamino-polyamide with a crosslinking agent, said polyamino-polyamide being prepared by the polycondensation of (a) an acidic compound selected from the group consisting of (i) organic dicarboxylic acid, (ii) ethylenically unsaturated aliphatic mono- or di-carboxylic acid, (iii) ester of said acids of (i) and (ii), and (iv) mixtures of (i), (ii) and (iii) on (b) a polyamine selected from the group consisting of bis-primary and mono- or bis-secondary polyalkylene polyamines, said polyamine (b) being replaceable by a member selected from the group consisting of (1) 0-20 mole percent hexamethylene diamine, (2) 0-40 mole percent bis-primary amine and (3) 0-40 mole percent bis-secondary amine, said crosslinking agent being selected from the group consisting of (a') simple bi-functional compounds selected from bis-halohydrins, bis-azetidinium, bis-haloacyl diamine and alkyl bis-halides, (b') oligomers obtained by the reaction of (1') a compound selected from the group consisting of the compounds in (a') above or an epihalohydrin, a bis-epoxide, or a bis-unsaturated derivative with (2') a compound reactive with the compound in (1'), and (c') the quaternized compounds comprising said crosslinked polymer alkylated with an alkylating agent selected from the group consisting of (a) epoxides, (b) ethylenically unsaturated compounds, (c) chloroacetic acid, and (d) alkane sultone selected from the group consisting of propane sultone and butane sultone. The crosslinking agent is employed in amounts of 0.025–0.35 mole per amine group in said polyamino-polyamide. The said crosslinked polymer is soluble in water in amounts of 10 weight percent thereof without essentially any gel formation and a 10 weight percent aqueous solution of the said crosslinked polymer has a viscosity greater than 3 centipoises at 25° C.

24 Claims, No Drawings

CROSSLINKED POLYAMINO-POLYAMIDE IN HAIR CONDITIONING COMPOSITIONS

This application is a continuation-in-part of our application Ser. No. 762,804, filed Jan. 26, 1977, which is a continuation of our application Ser. No. 528,577, filed Nov. 29, 1974, now abandoned.

BACKGROUND OF THE INVENTION

It is known that the hair of many people, because of its general condition or because of repeated exposure to the atmosphere or to treatments such as bleaching, permanent wavings or dyeings, becomes degraded and often difficult to comb out or to set, especially in the case of a thick head of hair which is often dry, dull, rough or lacks vigor and liveliness.

Efforts heretofore have been made to limit or to correct these faults by applying to the air a "hair conditioner" composition so as to improve the condition of moist and dry hair and to facilitate such operations as combing and setting the hair.

By "hair conditioning" is meant an operation which, while facilitating the combing out of moist hair, also imparts to dry hair some swelling and elasticity, so as to assure good maintenance of the coiffure or style imparted thereto. The agents employed to achieve such "hair conditioning" are generally called "hair conditioners".

Conventionally there is employed in the conditioning of hair various synthetic polymers, such as polyethylene imines, polyvinylpyridines, the polychloride of p-vinylbenzyl trimethylammonium and the polychloride of diallyl dimethyl ammonium. However, it has also been found that these polymers suffer from the disadvantages of not being compatible with, for instance, anionic shampoo compositions.

It has also been known to use in the production of compositions for hair some polyamino-amide polymers, obtained by the polycondensation of a dicarboxylic acid and a polyalkylene polyamine, some polyaminourethylene polymers and some alkylene polyamine polymers modified particularly by epichlorohydrin in quantities near stoichiometric amounts relative to the amine groups of the polyamino-amide. However, the addition of these significant quantities of epichlorohydrin leads to the presence in the molecules of the crosslinked polymer some reactive groups. These polymers thus contained alkylating groups which are capable of reacting on nucleophilic groups such as amines, thiols, sulfates and the like. Representative of such alkylating groups are azetidinium rings. However, as a result of the presence of such reactive groups, the polymer lacks stability and generally degrades when put into solution. Further the presence of such alkylating groups renders cosmetic products incorporating the same of doubtful use for application to human skin.

There has also been recommended the use in a "hair conditioner" composition of heat crosslinkable thermosetting polymers, but their use necessarily involves a special heating step.

To avoid these drawbacks, there has been provided in our earlier applications Ser. Nos. 762,804 and 528,577, incorporated herein by reference, a chemically stable, crosslinked polyamino-polyamide free from reactive groups. This water-soluble crosslinked polymer is obtained by crosslinking a polyamino-polyamide which in turn is prepared by the polycondensation of an acidic compound on a polyamine. The acidic compound used is selected from the group consisting of:

(i) an organic dicarboxylic acid,
(ii) an ethylenically unsaturated aliphatic mono- or di-carboxylic acid,
(iii) an ester and said acids, preferably with a lower alkanol having from 1-6 carbon atoms, and
(iv) mixtures of these compounds.

The polyamine usefully employed to produce the polyamino-polyamide of our earlier applications is selected from the group consisting of bis-primary and mono- or bis-secondary polyalkylene-polyamines. From 0-40 mole percent of the selected polyamine can be replaced by a bis-primary amine, preferably, ethylenediamine or by a bis-secondary amine, preferably piperazine and 0-20 mole percent of the selected polyamine can be replaced by hexamethylene-diamine.

Crosslinking of the polyamino-polyamide in our earlier applications is effected with a crosslinking agent selected from the group consisting of epihalohydrins, diepoxides, dianhydrides, unsaturated anhydride and bis unsaturated derivatives, and is characterized by the fact that the crosslinking agent is employed in amounts of 0.025–0.35 mole of crosslinking agent per amine group of the polyamino-polyamide and generally from 0.025 up to about 0.2 mole and, in particular, from 0.025 to up to about 0.1 mole of crosslinking agent per amine group of the polyamino-polyamide.

Our earlier invention, as described in said Serial Nos. 762,804 and 528,577 is also concerned with a hair conditioning cosmetic composition which comprises at least one water-soluble crosslinked polymer as defined above. This cosmetic composition is compatible with anionic shampoo compositions; it provides satisfactory combing out of moist hair and it imparts elasticity to dry hair thereby assuring good maintenance of the coiffure or style imparted to the hair.

The crosslinked polyamino-polyamide present in the hair conditioning composition of our earlier invention exhibits the following characteristics: (1) it is perfectly soluble in water up to 10 weight percent concentration without forming a gel, (2) the viscosity of such a 10% solution in water at 25° C. is greater than 3 centipoises, the viscosity generally measuring between 3–200. More often the viscosity of such a solution is equal to or greater than 20 centipoises and lower than 50 centipoises; and (3) the polyamino-polyamide does not carry any reactive group and in particular it is chemically stable and does not have any alkylating characteristics.

DESCRIPTION OF THE INVENTION

The present invention is an improvement over our invention disclosed in said Ser. Nos. 762,804 and 528,577. Thus, it has now been found that by using different crosslinking agents, new crosslinked polyamino-polyamide polymers, as well as new cosmetic compositions for the hair containing these new polymers have now been provided.

In accordance with the present invention, the new polymers and the new compositions containing them exhibit relative to the polymers and to the hair compositions described in our earlier applications the advantage of imparting to the hair a better cosmetic state and principally of imparting to dry hair more body and elasticity, and improving or prolonging the maintenance of the hair style.

This advantage is more significant in the case of damaged hair having been submitted to successive bleachings and/or permanent wave treatments.

The new crosslinking agents employed in the present invention can be classified into the following three groups:

I—Simple bi-functional compounds selected from the group consisting of bis-halohydrins, bi-azetidinium, bis-haloacyl diamines and bis-alkyl halides;

II—Oligomers obtained by the reaction of compound (a) selected from the group consisting of the bi-functional compounds described in Group I above and the bi-functional crosslinking agents described in our earlier applications, i.e. epihalohydrins, bis-epoxides and bis-unsaturated derivatives, and specifically epichlorohydrin, N,N'-bis-epoxy propyl piperazine, diglycidyl ether, divinyl sulfone, methylene bis-acrylamide, on compound (b) which is a bi-functional compound reactive with compound (a);

III—The product of quaternization of a compound selected from the group consisting of compounds (a), described in the preceding paragraph, and the oligomers described in Group II which carry one or more tertiary amine groups totally or partially alkylatable with a known alkylating agent and in particular with an alkylating agent selected from the group consisting of chlorides, bromides, iodides, sulfates, mesylates and tosylates of methyl or ethyl, benzyl chloride or bromide, ethylene oxide, propylene oxide and glycidol.

More preferably the polymers of the present invention are produced using a crosslinking agent selected from the group consisting of (I) simple bi-functional compounds selected from the group consisting of (1) bis-halohydrins resulting from the reaction of epihalohydrin with a primary amine, a bis-secondarydiamine, a bis-phenol or a bis-mercaptan, (2) bis-azetidinium, (3) bis-haloacyl diamines, (4) alkyl bis-halides of the formula

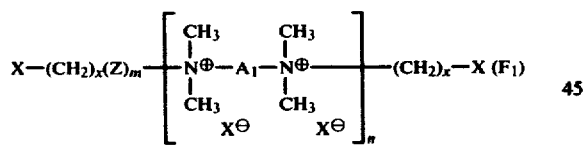

where
X = Cl or Br, Z represents

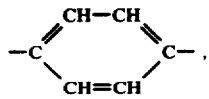

$x = 1$ to 3, $m = 0$ or 1, $n = 0$ or 1, $m$ and $n$ not representing 1 at the same time; moreover, when $m = 1$, $x = 1$; $A_1$ represents a saturated divalent hydrocarbon radical having 2, 3, 4 or 6 carbon atoms or 2-hydroxy propylene;

(II) oligomers obtained by the reaction of compound (a) selected from the group consisting of compounds (1), (2), (3), (4), each identified above, (5) epihalohydrins, (6) bis-epoxides and (7) bis-unsaturated derivatives with compound (b) which is a bi-functional compound reactive with compound (a) and selected from the group consisting of primary amines, bis-secondary diamines, bis-mercaptans and bis-phenols; the molar ratio of (b):(a) being between 0.1 and 0.9;

(II-bis) oligomers obtained by the reaction of compound ($a_1$) selected from the group consisting of compounds (1), (3), (4) and (6) each identified above with a bis-tertiary diamine ($b_1$) which is a bi-functional compound reactive with compound ($a_1$); the molar ratio ($b_1$):($a_1$) being between 0.1 and 0.9;

(III) the product of quaternization of a compound ($a_2$) selected from the group consisting of (1) bis-halohydrins resulting from the reaction of a epihalohydrin with piperazine, a bis-phenol or a bis-mercaptan, (2) bis-azetidinium, (3) bis-haloacyl diamines, (4) alkyl bis-halides of formula $F_1$, above, (6) bis-epoxides, (7) bis-unsaturated derivatives, (8) oligomers of II above, obtained by the reaction of compound ($a_3$) selected from the group consisting of compounds (1), (2), (3), (4), (6) and (7) each identified above with compound ($b_3$) which is a bi-functional compound reactive with compound ($a_3$) and selected from the group consisting of primary amines, bis-secondary diamines, bis-mercaptans and bis-phenols, the molar ratio ($b_3$):($a_3$) being between 0.1 and 0.9, (9) oligomers obtained by the reaction of an epihalohydrin (compound $a_4$) with a bi-functional compound ($b_4$) selected from piperazine, bis-mercaptans, bis-phenols and bis-epoxides of piperazine, the molar ratio of ($b_4$):($a_4$) being between 0.1 and 0.9; (10) oligomers obtained by the reaction of compound ($a_5$) selected from the group consisting of (1) bis-halohydrins resulting from the reaction of an epihalohydrin with piperazine, a bis-phenol or a bis-mercaptan, (2) bis-haloacyl diamines, (3) alkyl bis-halides of formula $F_1$, above, and (4) bis-epoxides, with compound ($b_5$) which is a bis-tertiary diamine, the molar ratio ($b_5$):($a_5$) being between 0.1 and 0.9; the said product having at least one tertiary amine group which is alkylatable, with an alkylating agent (c) selected from the group consisting of chlorides, bromides, iodides, sulfates, mesylates and tosylates of methyl or ethyl, benzyl chloride or bromide, ethylene oxide, propylene oxide and glycidol.

The simple bi-functional compounds of Group I are more specifically:

(1') bis-halohydrins obtained by the reaction of an epihalohydrin, such as epichlorohydrin or epibromohydrin with a bi-functional compound such as bis-secondary diamines, primary amines, diols, bis-phenols or bis-mercaptans. These bis-halohydrins form very valuable crosslinking agents.

The bis-halohydrin resulting from the reaction of epichlorohydrin with piperazine is particularly valuable.

The bis-halohydrins can be direct intermediates for the preparation of bis-epoxides, but, inversely, they can be derived by opening the oxirane ring with an hydracid such as hydrochloric acid or hydrobromic acid.

In both cases, the halogen atom can be linked at the last carbon atom or the next-to-last carbon atom without its position being prejudicial to the reactivity of the crosslinking agent or to the properties of the final product.

Representative useful bis-halohydrins include the following:

$$X-CH_2-CH-CH_2 \left[ N\underset{\diagdown \_\_ \diagup}{\overset{\diagup \_\_ \diagdown}{}}N-CH_2-CH-CH \right]_n X, \quad (1)$$
$$\quad\quad\quad\quad OH \quad\quad\quad\quad\quad\quad\quad\quad\quad\quad\quad OH$$

n = 1 to 4;

$$X-CH_2-CHOH-CH_2-N\underset{\diagdown \_\_ \diagup}{\overset{\diagup \_\_ \diagdown}{}}N-CH_2-CHOH-CH_2-N\underset{\diagdown \_\_ \diagup}{\overset{\diagup \_\_ \diagdown}{}}N-CHOH-CH_2-X; \quad (2)$$

$$X-CH_2-CHOH-CH_2-\underset{CH_3}{\overset{|}{N}}-(CH_2)_n-\underset{CH_3}{\overset{|}{N}}-CH_2-CHOH-CH_2-X, \quad n = 2-6; \quad (3)$$

$$X-CH_2-CHOH-CH_2-\underset{R}{\overset{|}{N}}-CH_2-CHOH-CH_2X, \quad R = C_nH_{2n+1} \text{ or} \quad (4)$$

$$-(-CH_2-CH_2-O-)_{\overline{m}}, \quad n = 1-18 \text{ and } m = 1 \text{ or } 2;$$

$$X-CH_2-CHOH-CH_2-O-(-CH_2-CH_2-O-)_{\overline{p}}CH_2-CHOH-CH_2X, \quad p = 0-25; \quad (5)$$

$$X-CH_2-CHOH-CH_2-O-\underset{\text{phenyl}}{\bigcirc}-\underset{CH_3}{\overset{CH_3}{\underset{|}{C}}}-\underset{\text{phenyl}}{\bigcirc}-O-CH_2-CHOH-CH_2X; \quad (6)$$

and $$X-CH_2-CHOH-CH_2-S-(CH_2)_q-S-CH_2-CHOH-CH_2X, \quad q = 2-6; \quad (7)$$

and in the formulas (1)–(7), X represents Cl or Br.

(2′) bis-azetidinium compounds derived from N,N-dialkyl halogeno hydroxy propylamines by cyclization. A representative bis-azetidinium is one made in accordance with the following reaction scheme:

$$X-CH_2-CHOH-CH_2-N\underset{\diagdown \_\_ \diagup}{\overset{\diagup \_\_ \diagdown}{}}N-CH_2-CHOH-CH_2-N\underset{\diagdown \_\_ \diagup}{\overset{\diagup \_\_ \diagdown}{}}N-CH_2-CHOH-CH_2X$$

$$\longrightarrow HO-\underset{\overset{\oplus}{X\ominus}}{\triangleleft N \triangleright}N\underset{\diagdown \_\_ \diagup}{\overset{\diagup \_\_ \diagdown}{}}N-CH_2-CHOH-CH_2-N\underset{\diagdown \_\_ \diagup}{\overset{\diagup \_\_ \diagdown}{}}N\underset{\overset{\oplus}{X\ominus}}{\triangleleft N \triangleright}-OH,$$

wherein X represents Cl or Br.

However, the cyclization can be difficult for certain sterically hindered amines.

As the reactivity of the azetidinium groups is only slightly different from that of epihalohydrin groups, there can be employed in the present invention compounds derived from bis-halohydrins for which the halohydrin units are linked to the remainder of the molecule by tertiary nitrogen groups, and carry two azetidinium groups or one azetidinium group and one halohydrin group;

(3′) bis-haloacyl diamines useful as crosslinking agents can be represented by the formula:

$$X-(CH_2)_n-CON-A-N-CO-(CH_2)_nX,$$
$$\quad\quad\quad\quad\quad\quad |\quad\quad |$$
$$\quad\quad\quad\quad\quad\quad R_1\quad\quad R_2$$

wherein X = Cl or Br, A = —CH$_2$—CH$_2$—, $$-CH_2-CH_2-CH_2- \quad \text{or} \quad -\overset{O}{\underset{\|}{C}}-,$$

n represents a number between 1 and 10, $R_1 = R_2 = H$ or $R_1$ and $R_2$ can be linked together and represent an ethylene radical; when $$A = -\overset{O}{\underset{\|}{C}}-,$$

$R_1 = R_2 = H$; when A represents —CH$_2$CH$_2$—, $R_1$ and $R_2$ can be linked together and represent ethylene so that the group $$-N-A-N-$$
$$\ \ |\quad\quad\ \ |$$
$$\ \ R_1\quad\ R_2$$

designates the radical $$-N\underset{\diagdown \_\_ \diagup}{\overset{\diagup \_\_ \diagdown}{}}N-$$

which can be derived from piperazine.

Particularly useful bis-haloacyl diamines in the invention are the bis-chloroacetyl or the bis-bromo undecanoyl of ethylenediamine or of piperazine.

Particularly useful bis-epoxides are bis-epoxydes of piperazine;

(4') oligomers, within the meaning of the present invention, are statistical mixtures of compounds obtained by the reaction of compound (a) described in Groups I and II or of a compound ($a_1$) described in Group II-bis or of a compound ($a_3$), ($a_4$) or ($a_5$) described in Group III with, respectively, a bi-functional compound (b), ($b_1$), ($b_3$), ($b_4$), ($b_5$) which are reactive with compounds (a), ($a_1$), ($a_3$), ($a_4$), ($a_5$) which are in a general fashion, primary amines, bis-secondary amines such as piperazine, bis-tertiary diamines such as N,N,N',N'-tetramethyl ethylene-, propylene-, butylene-, or hexamethylene-diamine, bis-mercaptans such as ethane 1,2-dithiol, or the bis-phenols such as Bis-phenol A or 2,2'-(4,4'-dihydroxy-diphenyl) propane.

The molar amount of (b), ($b_1$), ($b_3$), ($b_4$), ($b_5$), relative, respectively, to (a), ($a_1$), ($a_3$), ($a_4$), ($a_5$) is between 0.1 and 0.9.

The oligomerization reaction is generally carried out at temperatures between 0° and 95° C. and preferably between 0° and 50° C. in water, or in a solvent such as isopropanol, t-butanol, acetone, benzene, toluene, dimethylformamide or chloroform.

The quaternization reaction which provides the quaternization product described above, under III, is effected between 0° and 90° C. in water or in a solvent such as methanol, ethanol, isopropanol, t-butanol, alkoxy ethanols, acetone, benzene, toluene, diamethylformamide or chloroform.

Thus, the present invention relates to a crosslinked polyamino-polyamide polymer prepared by crosslinking a polyamino-polyamide, obtained by the polycondensation of an acidic compound selected from (i) organic dicarboxylic acids, (ii) aliphatic ethylenically unsaturated mono- and di-carboxylic acids, (iii) the esters of the said acids and (iv) mixtures of these compounds, on a polyamine selected from bis-primary and mono- or di-secondary polyalkylene-polyamines, 0 to 20 mole percent of this polyamine being able to be replaced by hexamethylene diamine, or 0 to 40 percent of this polyamine being able to be replaced by a bis-primary amine, preferably, ethylene diamine, or by a bis-secondary amine, preferably, piperazine. The crosslinking is effected using a crosslinking agent selected from the group consisting of:

(I) simple bi-functional compounds selected from the group consisting of (1) bis-halohydrins resulting from the reaction of an epihalohydrin with a primary amine, a bis-secondary diamine, a bis-phenol or a bis-mercaptan (2) bis-azetidinium, (3) bis-haloacyl diamines, (4) alkyl bis-halides represented by the formula:

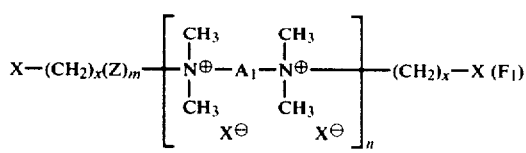

wherein X=Cl or Br, Z represents

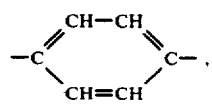

$x = 1$ to 3, $m = 0$ or 1, $n = 0$ or 1, m and n at the same time not representing 1; moreover when $m = 1$, $x = 1$; $A_1$ represents a divalent saturated hydrocarbon having 2, 3, 4 or 6 carbon atoms or 2-hydroxy propylene;

(ii) oligomers obtained by the reaction of compound (a) selected from the group consisting of compounds (1), (2), (3), (4), each identified above, (5) epihalohydrins, (6) bis-epoxides and (7) bis-unsaturated derivatives; with compound (b) which is a bi-functional compound reactive with compound (a) and selected from the group consisting of primary amines, bis-secondary amines, bis-mercaptans and bis-phenols;

(II-bis) oligomers obtained by the reaction of compound ($a_1$) selected from the group consisting of compounds (1), (3), (4) and (6) each identified above with a bis-tertiary diamine ($b_1$) which is a bi-functional compound reactive with compound ($a_1$); the molar ratio ($b_1$):($a_1$) being between 0.1 and 0.9;

(III) the product of quaternization of compound ($a_2$) selected from the group consisting of (1) bis-halohydrins resulting from the reaction of an epihalohydrin with piperazine, a bis-phenol or a bis-mercaptan, (2) bis-azetidinium, (3) bis-haloacyl diamines, (4) alkyl bis-halides of formula $F_1$, (6) bis-epoxides, (7) bis-unsaturated derivatives, (8) oligomers II obtained by the reaction of compound ($a_3$) selected from the group consisting of compounds (1), (2), (3), (4), (6) and (7) each identified above with compound ($b_3$) which is a bi-functional compound reactive with compound ($a_3$) and selected from the group consisting of primary amines, bis-secondary diamines, bismercaptans and bis-phenols, the molar ratio ($b_3$):($a_3$) being between 0.1 and 0.9, (9) oligomers obtained by the reaction of an epihalohydrin (compound $a_4$) with a bi-functional compound ($b_4$) selected from piperazine, bis-mercaptans, bisphenols, bis-epoxides of piperazine; the molar ratio of ($b_4$):($a_4$) being between 0.1 and 0.9; (10) oligomers obtained by the reaction of a compound ($a_5$) selected from the group consisting of (1) bis-halohydrins resulting from the reaction of an epihalohydrin with piperazine, a bis-phenol or a bismercaptan, (2) bis-haloacyl diamines, (3) alkyl bis-halides of formula $F_1$ and (4) bis-epoxides with compound ($b_5$) which is a bis-tertiary diamine, the molar ratio ($b_5$):($a_5$) being between 0.1 and 0.9; said product having at least one tertiary amine group alkylatable with an alkylating agent (c) selected from the group consisting of chlorides bromides, iodides, sulfates, mesylates and tosylates of methyl or ethyl, benzyl chloride or bromide, ethylene oxide, propylene oxide and glycidol.

The acids useful for the preparation of the polyamino-polyamide of the present invention are selected from organic saturated dicarboxylic acids having from 6 to 10 carbon atoms, for example adipic acid, 2,2,4-trimethyl and 2,4,4-trimethyl adipic acids; terephthalic acid; aliphatic ethylenically unsaturated mono- and di-carboxylic acids, for example, acrylic acid, methacrylic acid and itaconic acid.

Among the preferred acids are adipic acid and the addition compounds of an alkylene diamine with an unsaturated acid such as acrylic acid, methacrylic acid and itaconic acid.

Adipic acid is particularly preferable.

The esters of the above mentioned acids can also be used. It is also possible to use mixtures of two or more carboxylic acids and their esters.

The polyamines useful for the preparation of the polyamino-polyamide of the present invention are selected from bis-primary or mono- or di-secondary polyalkylenepolyamines, for example, diethylene triamine, dipropylene triamine, triethylene tetramine and their mixtures.

The polycondensation is carried out in accordance with known procedures, by mixing the initial reactants; heating the resulting mixture to a temperature between 80° and 250° C., and preferably between 100° and 180° C., for 1 to 8 hours. The choice of the exact reaction time and temperature can depend on the choice of the particular reactants selected but the same is easily determined by those skilled in the art. After heating the reaction mixture at total reflux for 178 hour to 1 hour, the water or alcohol formed during the course of the polycondensation is removed at first at atmospheric pressure and then at subatmospheric pressure.

The polycondensation reaction is carried out under a nitrogen atmosphere to avoid any significant colorations and to facilitate the elimination of volatile substances.

In carrying out the polycondensation reaction preferably equimolar amounts of the dicarboxylic acid and amine are employed.

According to a preferred embodiment of the present invention, the polycondensation of the polyalkylenepolyamine selected preferably from diethylene triamine, triethylene tetramine, dipropylene triamine and mixtures thereof is effected with either (i) a carboxylic diacid, preferably adipic acid or its dimethyl ester, or (ii) the intermediate product of addition of one molecule of ethylene diamine and two molecules of the methyl ester of an ethylenically unsaturated acid such as methyl acrylate or methyl itaconate.

The addition reaction of ethylene diamine on the said unsaturated ester is carried out by mixing the reactants at a temperature between 5°–80° C. The polycondensation reaction is effected by heating the reactants for 30–60 minutes at reflux followed by eliminating the methyl alcohol formed, at a temperature of 120°–150° C., or of the water formed at a temperature of 140°–175° C., initially under atmospheric pressure and finally under sub-atmospheric pressure of 15 mm of mercury.

The polyamino-polyamides (A) thus obtained have a viscosity in a 10% aqueous solution at 25° C. lower than 3 centipoises.

The preferred polyamino-polyamides (A) of the present invention are characterized by repeating units of the formula $$-\!\!+\!\!OC\!-\!R\!-\!CO\!-\!Z\!-\!\!+\!\!-\quad (I)$$

wherein R represents a bivalent radical which is derived from the acid employed or from the addition product of the acid with a bis-primary or bis-secondary amine.

Representative preferred values for R includes

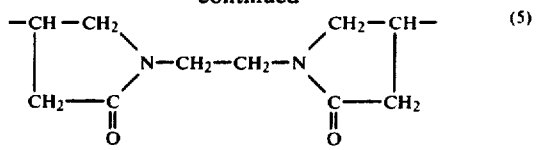 (1)

$-(CH_2)_4-$, (2)
$-CH_2CH_2-NH-CH_2-CH_2-NH-CH_2CH_2-$, (3)
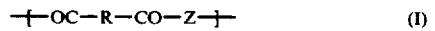 and (4)

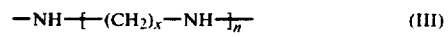 (5)

These radicals are derived, respectively, from terephthalic acid, adipic acid, the product of addition of ethylenediamine with acrylic acid, methacrylic acid and itaconic acid, or their esters;

Z is selected from the group consisting of:

(1) in amounts of 60–100 mole percent, the radical $$-NH\!\!-\!\!+\!\!-(CH_2)_x\!-\!NH\!-\!\!+\!\!_n\!\!-\quad (III)$$

wherein (a) x=2 and n=2 or 3 or (b) x=3 and n=2, this radical being derived from diethylene triamine, triethylene tetramine or dipropylene triamine;

(2) in amounts of 0–40 mole percent (a) the radical (II) above, in which X=2 and n=1, the said radical being derived from ethylenediamine, or (b) the radical

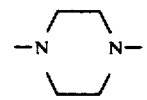

which is derived from piperazine; and (3) in amounts of 0–20 mole percent the radical —NH—(CH$_2$)$_6$—NH— which is derived from hexamethylenediamine.

The polyamino-polyamides thus obtained are then crosslinked by the addition of a crosslinking agent selected from those described above.

The crosslinking reaction is effected at a temperature between 20° C. and 90° C. using initially 20 to 30% aqueous solutions of the polyamino-polyamide to which is added the crosslinking agent by very small fractions until there is obtained a significant increase in the viscosity, but without, however, forming a gel which no longer is soluble in water. The concentration is then rapidly adjusted to 10% by the addition of water and the reaction mixture is then cooled.

According to a preferred characteristic of the present invention, there is employed during the crosslinking of the polyamino-polyamide polymers, a crosslinking agent in amounts of 0.025 to 0.35 mole per amine group of the polyamino-polyamide. An interesting category of crosslinked polymers is obtained by using from 0.025 to up to about 0.2 mole of crosslinking agent per amine group of the polyaminopolyamide. Another advantageous category of crosslinked polymers is obtained by using from 0.025 to up to about 0.1 mole of crosslinking agent per amine group of the polyaminopolyamide.

The amount of crosslinking agent to use, which can vary according to the nature of the polyamino-polyamide and of the crosslinking agent can be easily determined by adding the desired crosslinking agent to an aqueous solution of the polyamino-polyamide until the viscosity of a 10% solution is at 25° C. between 3 centipoises and the gel state while preserving its perfect solubility in water.

The crosslinked polymers according to the present invention keep well and are compatible with anionic surfactants while providing good untangling of wet hair. This compatibility with anionic surfactants can again be improved by alkylation of the secondary amine groups of the crosslinked polyamino-polyamides. The alkylation improves the water solubility of the crosslinked polyamino-polyamides, in the presence of anionic surfactants.

The following alkylating agents can be employed:
(1) an epoxide, for example, glycidol, ethylene oxide, or propylene oxide,
(2) an ethylenically unsaturated compound, for example, acrylamide and acrylic acid;
(3) chloroacetic acid; and
(4) an alkane sultone, for example, propane sultone or butane sultone.

The alkylation of the crosslinked polyaminoamides is carried out in an aqueous solution, at a concentration of 10 to 30% and at a temperature between 10° and 95° C.

The crosslinked polymers according to the present invention can be used in various cosmetic compositions for the hair, for the treatment of normal hair and more particularly for the treatment of sensitized hair. They can also be used in concentrations from 0.1 to 5 weight percent, preferably, from 0.2 to 2.5 weight percent and advantageously, from 0.3 to 1.3 weight percent in cosmetic compositions for the hair and more particularly in shampoo compositions, such as an anionic, cationic, non-ionic, amphoteric or zwitterionic shampoo composition, a shampoo-dye composition, a hair dye composition, a hair styling gel, a hair styling lotion, a "brushing" lotion, a hair setting lotion, a hair rinse lotion, a non-rinse hair reinforcing setting lotion, a hair restructuring lotion, and in such cosmetic compositions as anti-pellicular and anti-seborrheic compositions and permanent waving compositions.

The present invention thus also relates to a cosmetic composition for the hair containing at least one water-soluble crosslinked polymer obtained by crosslinking a polyamino-polyamide prepared by the polycondensation of an acid compound selected from (i) organic dicarboxylic acids, (ii) aliphatic ethylenically unsaturated mono- and di-carboxylic acids, (iii) esters of the said acids and (iv) mixtures of these compounds, on a polyamine selected from bis-primary and mono- or di-secondary polyalkylene-polyamindes, 0 to 20 mole percent of this polyamine being able to be replaced by hexamethylene diamine, or 0 to 40 percent of this polyamine being able to be replaced by a bis-primary amine, preferably, ethylene diamine or by a bis-secondary amine, preferably, piperazine; the crosslinking being carried out with the use of a crosslinking agent selected from the group consisting of (I) a compound selected from the group consisting of (1) bis-halohydrins, (2) bis-azetidinium, (3) bishaloacyl diamines and (4) alkyl bis-halides;

(II) oligomers obtained by the reaction of compound (a) selected from the group consisting of (1) bis-halohydrins, (2) bis-azetidinium, (3) bis-haloacyl diamines, (4) alkyl bis-halides, (5) epihalohydrins, (6) bis-epoxides and (7) bis unsaturated derivatives, with compound (b) which is a bi-functional compound reactive with compound (a);

(III) the product of quaternization of a compound selected from the group consisting of compound (a) and oligomers (II) and carrying tertiary amine groups alkylatable with an alkylating agent (c) selected from the group consisting of the chlorides, bromides, iodides, sulfates, mesylates and tosylates of methyl or ethyl, benzyl chloride or bromide, ethylene oxide, propylene oxide and glycidol.

The crosslinking is advantageously carried out by means of a crosslinking agent selected from the group consisting of:

(I) simple bi-functional compounds selected from the group consisting of (1) bis-halohydrins resulting from the reaction of an epihalohydrin with a primary amine, a bis-secondary amine, a bis-phenol or a bis-mercaptan, (2) bis-azetidinium, (3) a bis-haloacyl diamine, (4) an alkyl bis-halide having the formula

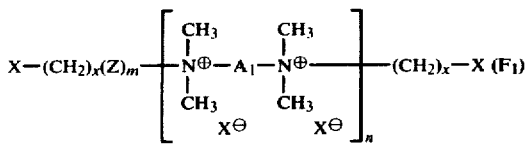

wherein X = Cl or Br, Z represents

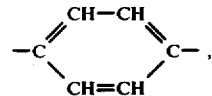

X = 1 to 3, m = 0 or 1, n = 0 or 1, m and n not representing 1 at the same time; moreover, when m = 1, x = 1; A$_1$ represents a saturated divalent hydrocarbon radical having 2, 3, 4 or 6 carbon atoms or 2-hydroxy propylene;

(II) oligomers obtained by the reaction of compound (a) selected from the group consisting of compounds (1), (2), (3) and (4) each identified above, (5) epihalohydrins, (6) bis-epoxides and (7) bis-unsaturated derivatives with compound (b) which is a bi-functional compound reactive with compound (a) and selected from the group consisting of primary amines, bis-secondary diamines, bis-mercaptans and bis-phenols; the molar ratio (b):(a) being between 0.1 and 0.9;

(II-bis) oligomers obtained by the reaction of compound (a$_1$) selected from the group consisting of compounds (1), (3), (4), and (6) each identified above with a bis-tertiary diamine (b$_1$) which is a bi-functional compound reactive with compound (a$_1$); the molar ratio (b$_1$):(a$_1$) being between 0.1 and 0.9;

(III) the product of quaternization of compound (a$_2$) selected from the group consisting of (1) bis-halohydrins resulting from the reaction of an epihalohydrin with piperazine, bis-phenols or bis-mercaptans, (2) bis-azetidinium, (3) bis-haloacyl diamines, (4) alkyl bis-halides of formula F$_1$ above, (6) bis-epoxides, (7) bis-unsaturated derivatives, (8) oligomers II obtained by the reaction of compound (a$_3$) selected from the group consisting of compounds (1), (2), (3), (4), (6), and (7) each identified above with compound (b$_3$) which is a bi-functional compound reactive with compound (a$_3$) and is selected from the group consisting of primary amines, bis-secondary diamines, bis-mercaptans and bis-phenols, the molar ratio (b$_3$):(a$_3$) being between 0.1 and 0.9, (9) oligomers obtained by the reaction of an epihalohydrin (compound a$_4$) with a bi-functional compound (b$_4$) selected from piperazine, bis-mercaptans, bis-phenols and bis-epoxides of piperazine, the molar ratio of (b$_4$):(a$_4$) being between 0.1 and 0.9; (10) oligomers obtained by the reaction of compound (a$_5$) selected from the group consisting of (1) bis-halohydrins resulting from the reaction of an epihalohydrin with piperazine, a bis-phenol or a bis-mercaptan, (2) bis-haloacyl diamines, (3) alkyl bis-halides of formula $F_1$ above, and (4) bis-epoxides, with compound ($b_5$) which is a bis-tertiary diamine, the molar ratio ($b_5$):($a_5$) being between 0.1 and 0.9; said product carrying tertiary amine groups alkylatable with an alkylating agent (c) selected from the group consisting of the chlorides, bromides, iodides, sulfates, mesylates and tosylates of methyl or ethyl, benzyl chloride or bromide, ethylene oxide, propylene oxide and glycidol.

The cosmetic composition is characterized by the fact that the polyamino-polyamide is crosslinked by means of 0.025 to 0.35, or better from 0.025 to about 0.2, or even better from 0.025 to about 0.1 mole of crosslinking agent per amine group of the polyamino-polyamide. The crosslinked polymer in the cosmetic composition of the present invention exhibits a combination of the following characteristics:

(1) it is perfectly soluble in water at 10% without formation of a gel;

(2) the viscosity of a 10% solution of polymerin water at 25° C. is greater than 3 centipoises; and (3) it does not have any reactive groups and in particular it does not have any alkylating properties and it is chemically stable.

The cosmetic compositions for the hair containing the crosslinked polymer of the present invention can have a pH between 2 and 11 and preferably between 3 and 8.

The cosmetic compositions for the hair according to the present invention before being applied to sensitized hair can include, advantageously, an electrolyte. The presence of the electrolyte in the composition reduces or suppresses the tendency sensitized hair has to fix durably the polymers. Representative useful electrolytes include water-soluble alkali or alkaline earth salts of mineral or organic acids and preferably the chlorides and acetates of sodium, potassium, ammonium and calcium. The amount of electrolyte is not critical. Preferably the electrolyte is present in an amount between 0.01 and 5 weight percent and advantageously from 0.4 to 3 weight percent of the total weight of the composition. The ratio of electrolyte:polymer is between 0:1 and 1.5:1.

The cosmetic compositions for the hair can be colored and thus contain from 0.001 to 0.5 weight percent of a dye based on the total weight of the composition. The cosmetic composition also conventionally contains a perfume in an amount of 0.1 to 0.5 percent by weight based on the total weight of the composition.

In the compositions of the present invention, the crosslinked polyamino-polyamide is present in an amount of 0.1 to 5 weight percent and preferably 0.1 to 3 weight percent based on the total weight of the composition.

The cosmetic compositions for the hair in accordance with the present invention can be provided in the form of aqueous or alcoholic solutions, the alcohol being a lower alkanol such as ethanol or isopropanol, or in the form of a cream, a gel, a dispersion, or an emulsion.

In addition to the crosslinked polyamino-polyamide, the cosmetic composition can include, generally, various adjuvants conventionally employed in cosmetic compositions for the hair. The adjuvants generally present in these cosmetic compositions are, for example, perfumes, dyes, preservatives, sequesterants, thickening agents, emulsifiers, anionic, cationic, amphoteric, zwitterionic or non-ionic surfactants, synergists, softening agents, cosmetic polymers or resins and in particular non-ionic or cationic polymers or resins.

The cosmetic compositions for the hair, according to the present invention, constitute principally treating creams to be applied to the hair before or after dyeing or bleaching the same, before or after shampooing the hair, before or after a permanent waving of the hair; hair dye products; shampoos; rinse lotions to be applied before or after a shampoo; hair setting lotions; brushing lotions; and hair structuring lotions.

When the compositions of the present invention constitute a treating cream to be applied before or after dyeing or bleaching the hair, before or after shampooing the hair, before or after a permanent waving of the hair, the carriers for these creams are formulated from soaps or a fatty alcohol in the presence of emulsifiers. They can also contain fatty amides, glycerine, polymers, perfumes and dyes.

The pH of these creams is between 3 and 9 and preferably between 5 and 9.

The soaps can be constituted from natural or synthetic fatty acids having 12–18 carbon atoms, such as lauric acid, myristic acid, palmitic acid, oleic acid, ricinoleic acid, stearic acid and isostearic acid, in concentrations between 10 and 30% and alkalizing agents such as NaOH, KOH, ammonia, monoethanolamine, diethanolamine and triethanolamine.

Representative fatty amides include, in particular, the following compounds: mono- or diethanolamides of acids derived from copra, from lauric acid or from oleic acid, in concentrations between 0 and 10%.

Representative fatty alcohols include, in particular, oleyl alcohol, tetradecyl alcohol, cetyl alcohol, stearyl alcohol and isostearyl alcohol, in amounts between 0 and 10%.

The creams can also be formulated with natural or synthetic alcohols having 12–18 carbon atoms in admixture with emulsifiers. Representative fatty alcohols include, in particular, the alcohol derived from the fatty acids of copra, tetradecyl alcohol, cetyl alcohol, stearyl alcohol and hydroxy stearyl alcohol, in concentrations between 5 and 25%.

Representative emulsifiers include the following:

non-ionic surfactants, such as oxyethylenated or polyglycerolated fatty alcohols, such as for example, oleyl alcohol polyoxyethylenated with 10 moles of ethylene oxide, cetyl alcohol oxyethylenated with 6 to 10 moles of ethylene oxide, cetyl stearyl alcohol oxyethylenated with 10 moles of ethylene oxide, stearyl alcohol oxyethylenated with 10–15 or 20 moles of ethylene oxide, oleyl alcohol polyglycerolated with 4 moles of glycerol and synthetic fatty alcohols having 9–15 carbon atoms polyoxyethylenated with 5 or 10 moles of ethylene oxide. These non-ionics are present in an amount of 5 to 25 weight percent;

anionic surfactants, such as alkyl sulfates oxyethylenated or not, including sodium lauryl sulfate, ammonium lauryl sulfate, sodium cetyl stearyl sulfate, triethanolamine cetyl stearyl sulfate, monoethanolamine lauryl sulfate, sodium lauryl ether sulfate oxyethylenated with, for example, 2.2 moles of ethylene oxide and monoethanolamine lauryl ether sulfate oxyethylenated with, for example, 2.2 moles of ethylene oxide. These constituents are present in an amount between 3 and 15 weight percent.

Representative fatty amides include oleic diethanolamide, copra mono- or di-ethanolamide and stearic monoethanolamide. These amides are used in amounts between 0 and 10 weight percent.

When the compositions of the present invention constitute hair dye creams, they can include, in addition to the crosslinked polyamino-polyamide, various components recited in the above defined creams which impart a cream consistency to the composition. There is also included an alkalizing agent and a hair dye.

The pH of these compositions is generally between 9 and 11, the pH being regulated by the addition of an appropriate alkalizing agent in the dye support. For example ammonia, monoethanolamine, diethanolamine or triethanolamine can be added to the dye support or vehicle.

The hair dyes are oxidation dyes to which can be added direct dyes such as an azo, an anthraquinone, or a nitrobenzene dye, an indamine, an indoaniline, an indophenol or other oxidation dyes such as the leuco derivatives of these compounds.

When the compositions of the present invention constitute shampoo formulations, they include, in addition to the crosslinked polyamino-polyamide polymer, at least one anionic, cationic, non-ionic or amphoteric detergent.

Representative anionic surfactants include the following compounds, as well as their mixtures:

the alkaline salts, the magnesium salts, the ammonium salts, the amine salts or the amino alcohol salts of the following compounds:

alkyl sulfates, alkyl ether sulfates wherein the alkyl have a $C_{12}$ to $C_{18}$ linear chain, ethoxylated alkylamide sulfates and ether sulfates with linear $C_{12}$ to $C_{18}$ chains, alkylaryl polyether sulfates and monoglyceride sulfates;

alkylsulfonates wherein the alkyl has a $C_{12}$ to $C_{18}$ linear chain, alkylamide sulfonates, alkylarylsulfonates and α-olefin sulfonates having $C_{12}$ to $C_{18}$ linear chains;

alkylsulfosuccinates, alkylethersulfosuccinates, and alkylamidesulfosuccinates wherein the alkyl moiety is a $C_{12}$-$C_{18}$ linear chain;

alkylsulfosuccinamates wherein the alkyl moiety is a $C_{12}$ to $C_{18}$ linear chain;

alkylsulfoacetates wherein the alkyl is a $C_{12}$ to $C_{18}$ chain;

alkyl phosphates and alkyletherphosphates wherein the alkyl is a $C_{12}$ to $C_{18}$ chain;

alkylsarcosinates, alkylpolypeptidates, alkylamidopolypeptidates, alkylisethionates and alkyl taurates wherein the alkyl is a $C_{12}$ to $C_{18}$ chain; and fatty acids such as oleic acid, ricinoleic acid, palmitic acid, stearic acid, the acids of copra oil, or of hydrogenated copra oil, carboxylic acids and carboxylic acids of polyglycol ethers of the formula Alk-)OCH$_2$—CH$_2$-)$_n$—OCH$_2$—CO$_2$H wherein Alk is a $C_{12}$ to $C_{18}$ liner chain and n is whole number from 5 to 15.

Representative cationic surfactants include, alone or in admixture, the following materials:

salts of fatty amines, such as alkylamine acetates;

quaternary ammonium salts, such as alkyl dimethylbenzylammonium chloride or bromide, alkyl trimethylammonium chloride or bromide, alkyl methylhydroxyethylammonium chloride or bromide, dimethyldistearylammonium chloride or bromide and methosulfates of alkylamido ethyltrimethylammonium chloride or bromide, salts of alkylpyridinium, and imidazoline derivatives.

Further, amine oxides having a cationic character such as alkyldimethylamine oxide or alkylaminoethyl dimethylamine oxide can also be used.

Representative non-ionic surfactants which can be used in admixture with the previously defined anionics, include:

condensation products of a mono alcohol, an α-diol, an alkylphenol or an amide with glycidol. Such products include, for example, compounds of the formula R—CHOH—CH$_2$—O—(CH$_2$—CHOH—CH$_2$—O)$_n$H, wherein R represents an aliphatic, cycloaliphatic or arylaliphatic radical having 7 to 21 carbon atoms and their mixtures, the aliphatic chains being able to have ether, thioether and hydroxymethylene groups and $1 \leq n \leq 10$; and compounds of the formula RO-(-C$_2$H$_3$O(CH$_2$OH)-)$_n$H wherein R represents alkyl, alkenyl or alkaryl having from 8 to 22 carbon atoms, and n represents a number between 1 and 10;

alcohols, alkylphenols or polyglycerolated or polyethoxylated fatty acids having a linear fatty $C_8$ to $C_{18}$ chain carrying most often from 2 to 15 moles of ethylene oxide, for example lauryl alcohol polyoxyethylenated with 12 moles of ethylene oxide;

copolymers of the oxides or ethylene and propylene;

the condensates of ethylene oxide and propylene oxide on fatty alcohols;

polyethoxylated fatty amides;

polyethoxylated fatty amines;

ethanolamides;

esters of fatty acids of glycol;

esters of fatty acids of sorbitol; and esters of fatty acids of sucrose.

Representative amphoteric surfactants which can be used include principally:

alkylamino mono- and di-propionates;

betaines, such as N-alkyl betaines, N-alkylsulfobetaines and N-alkylamidobetaines; and cycloimidinium (alkylimidazolines).

All these detergents, as well as numerous others not mentioned here but nonetheless useful in the shampoos according to the present invention, are well known and are described in the literature.

The compositions of the present invention in the form of shampoos can also contain various adjuvants such as for example perfumes, dyes, preservatives, thickening agents, foam stabilizers, softening agents and cosmetic resins.

Representative foam stabilizers include fatty amides and particularly copra mono- or di-ethanolamides, and lauric mono- or di-ethanolamides.

In these shampoo formulations, the detergent concentration is generally between 3 and 50 weight percent relative to the total weight of the composition, and preferably from 3 to 20 weight percent, and the pH is generally between 3 and 9.

When the compositions of the present invention constitute lotions, they can be styling lotions, forming lotions (called "brushing lotions"), non-rinse reinforcing hair setting lotions, rinsing lotions (called "rinses") and the like.

By a "brushing lotion" is meant a lotion which is applied after shampooing and which improves the styling of the hair which is effected on damp or moist hair with the aid of a brush, during the drying of the hair with the aid of a hand dryer.

By a non-rinse reinforcing hair setting lotion is meant a lotion which is applied after shampooing and before setting the hair and which lotion is not rinsed from the hair. This lotion facilitates setting the hair and improves the durability of the hair set.

These lotions include, in an aqueous, alcoholic or hydroalcoholic solution at least one crosslinked polyamino-polyamide such as defined above. They can also contain:

film forming polymers such as polyvinylpyrrolidone, copolymers of vinylpyrrolidone and vinyl acetate, copolymers resulting from the polymerization of vinyl acetate and vinyl alkyl ether.

Representative preferred resins, include polyvinylpyrrolidone having a molecular weight of 10,000 to 70,000; copolymers of viylpyrrolidone (VP) and vinyl acetate (VA) having a molecular weight of 30,000 to 200,000, the VP:VA ratio being between 30:70 and 70:30, and terpolymers of methyl methacrylate (15-25%)-stearyl methacrylate (18-28%) and dimethylaminoethyl methacrylate (52-62%) quaternized or not by methyl sulfate.

The composition can also contain: quaternary polyvinylpyrrolidone copolymers, such as for example a polymer having a molecular weight in the order of 1,000,000 and sold under the mark "Gafquat 755; " and a polymer having a molecular weight in the order of 100,000 sold under the mark "Gafquat 734;"graft cationic copolymers resulting from the copolymerization of 3 to 95 weight percent N-vinylpyrrolidone, from 3 to 95 weight percent dimethylaminoethyl methacrylate and 2 to 50 weight percent polyethyleneglycol such as those described in French Pat. No. 76 15 948; corresponding essentially to U.S. patent application Ser. No. 690,783 filed May 27, 1976, now U.S. Pat. No. 4,047,888, cationic polymers resulting from the condensation of piperazine or its derivatives (1) on bi-functional compounds such as alkyl or alkyl aryl dihalides, bis-epoxides, epihalohydrins, and bis-unsaturated derivatives, (2) on a primary amine whoses two hydrogen atoms can be substituted and which function as a bi-functional compound; (3) both on an epihalohydrin and on a hydroxylated amine such as diglycolamine, 2-amino-2-methyl-1,3-propanediol or on an amino acid such as glycocoll, quaternized celluloses such as "JR 400".

In these lotions, the polymer concentration is generally between 0.1 and 5 weight percent and preferably between 0.1 and 3 weight percent and the pH is generally between 3 and 9.

By rinse lotion is meant a lotion that is applied to the hair before or after a hair dyeing or bleaching operation, before or after a shampooing, or between successive shampooings, before or after a permanent wave operation, so as to obtain a conditioning effect of the hair. Such a lotion is rinsed from the hair after a short contact time therewith.

These cosmetic rinse compositions of the present invention can be in the form of aqueous or hydroalcoholic solutions containing or not surface active agents, or emulsions, or gels. Further these rinse compositions can be pressurized in aerosol containers. The surfactants used in these rinse lotions are principally non-ionic or cationic surfactants such as those described in the shampoo compositions above and more particularly:

condensation products of a mono alcohol, an α-diol, an alkylphenol or an amide with glycidol; for example, compounds of the formula R—CHOH—CH$_2$—O—(CH$_2$—CHOH—CH$_2$O)$_n$H wherein R represents an aliphatic, cycloaliphatic or arylaliphatic radical having 7 to 21 carbon atoms and their mixtures, the aliphatic chains being able to have ether, thioether and hydroxymethylene groups and $1 \leq n \leq 10$; and compounds of the formula RO—[C$_2$H$_3$O(CH$_2$OH)]$_n$H wherein R represents alkyl, alkenyl or alkylaryl having 8 to 22 carbon atoms and n is 1 to 10;

alcohols, alkylphenols or fatty acids, polyethoxylated or polyglycerolated, having a C$_8$ to C$_{18}$ linear fatty chain, and having most often from 2 to 15 moles of ethylene oxide.

The concentration of the surfactant in the rinse lotion can vary from 0 to 7 weight percent.

An anionic or amphoteric surfactant can also be included in these rinse lotions.

When the compositions are provided in the form of emulsions, they can be non-ionic or anionic. The non-ionic emulsions are constituted by a mixture of oils, and/or waxes, fatty alcohols and polyethoxylated fatty alcohols, such as stearyl or cetyl stearyl alcohols polyoxyethylenated for example with 10 moles of ethylene oxide. Cationic surfactants such as for example those defined above can also be employed.

The anionic emulsions are constituted from soaps. Representative emulsions include the self-emulsifiable emulsion constituted by glycerine stearate, sold under the name IMWITOR 960K and emulsions constituted by a combination of glycerine monostearate with esters of citric acid or with fatty alcohols and lipopeptides or with alkaline stearates, sold respectively under the names LAMEFORM ZEM, PLM and NSM.

When the compositions are provided in the form of gels they contain thickening agents in the presence or not of solvents.

Representative thickening agents include sodium alginate or gum arabic or cellulose derivatives such as methyl cellulose, hydroxymethyl cellulose, hydroxyethyl cellulose, hydroxypropyl cellulose, carboxymethyl cellulose or carboxylic polymers such as the "Carbopols." Thickening of the lotions can also be obtained by using polyethylene glycols and stearates or distearates of polyethylene glycols, or by using phosphoric esters and amines.

The concentration of the thickening agent can vary from 0.5 to 30 weight percent and preferably from 0.5 to 15 percent.

The pH of these rinse lotions varies generally from 2 to 9.5.

When the compositions of the invention constitute restructuring lotions, they contain products which reinforce the keratin chain of the hair.

Such products include methylol derivatives such as those described in French Pat. Nos. 1,527,085 and 1,519,979 corresponding essentially to U.S. Pat. No. 3,773,056.

The following non-limiting examples are given to illustrate the present invention. Unless otherwise stated, all parts and percentages are by weight.

EXAMPLES OF PREPARATION

EXAMPLE A—Polycondensation of equimolar amounts of adipic acid and diethylene triamine.

The resulting polymer is characterized by the following unit:

To 619 g (6 moles) of diethylene triamine, there are added, with agitation and under a nitrogen atmosphere and over a 15 minute period, 876 g (6 moles) of adipic acid. The reaction mixture is then heated to 145°–150° C., the temperature at which condensation of water is observed. The reaction mixture is maintained at reflux for 45 minutes at which time the water is removed by distillation, initially at ambient pressure for 2 hours and then under reduced pressure (15 mm Hg) for 1 hour. The heating temperature increases progressively up to 170° C.

The product thus obtained is poured out hot. After cooling, the product is in the form of a hard and brittle resin. It is transparent, has a yellow green color and is completely soluble in water.

EXAMPLE Ia

Preparation of a quaternized crosslinking agent of the formula

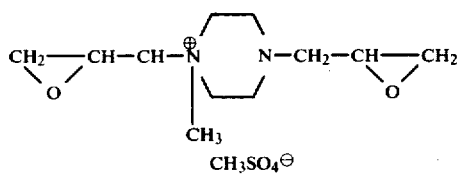

To 236 g of a chloroform solution containing 57.2 g (0.289 mole) of bis(epoxypropyl)piperazine, there are added, over a one hour period, 36.4 g (0.289 mole) of dimethyl sulfate while maintaining the reaction mixture under agitation at 30° C.

The quaternized derivative is then precipitated from its solution in a large excess of ether. After drying, there is recovered a very viscous oil, having an epoxide titer of 5.19 meq/g.

EXAMPLE Ib

Crosslinking, with the crosslinking agent in Example Ia, the polyamino-polyamide polymer obtained by condensation of adipic acid on diethylene triamine.

To 500 g of an aqueous solution containing 100 g (0.585 amine equivalent) of polyamino-polyamide prepared by condensation of equimolar amounts of adipic acid and diethylene triamine, according to Example A, there are added, at ambient temperature, 22 g (0.057 mole) of quaternized crosslinking agent prepared in Example Ia. The temperature of the reaction medium is then raised to 90° C.

After 20 minutes, gelling of the solution is observed. There are then rapidly added 698 g of water whereby a clear solution, yellow green in color, having 10% active material is obtained. The viscosity of this solution measured at 25° C. is 0.68 p at 86.93 sec.$^{-1}$.

EXAMPLE IIa

Preparation of a quaternized crosslinking agent of the formula

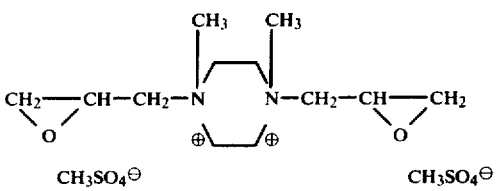

To 187.3 g of a chloroform solution containing 54.9 g (0.277 mole) of bis(epoxypropyl)piperazine, there are added, over a 1 hour period, 70 g (0.555 mole) of dimethyl sulfate, while maintaining the reaction medium under agitation at 30° C.

The medium thickened during the course of the addition and solidifies after several hours at ambient temperature. The paste is dissolved hot in dimethyl formamide. When cold, the solution gives up white crystals having a melting point of 205° C., for which the epoxide index is 4.25 meq/g.

EXAMPLE IIb

Crosslinking, with the crosslinking agent prepared in Example IIa, the polyamino-polyamide polymer obtained by the condensation of adipic acid on diethylene triamine.

To 476 g of an aqueous solution containing 95.2 g (0.557 amine equivalent) of the polyamino-polyamide prepared in Example A, there are added, at ambient temperature, 20 g (0.0425 mole) of the crosslinking agent prepared in Example IIa. The reaction mixture is maintained with agitation at 90° C. for 1 hour. Then the solution is adjusted to 10% active material by the addition of 656 g of water.

The solution is clear and has a yellow green color. Its viscosity, measured at 25° C. is 0.27 p at 87.98 sec.$^{-1}$.

EXAMPLE IIIa

Preparation of a bis-unsaturated oligomer crosslinking agent obtained from piperazine bis-acrylamide and piperazine in molar proportions of 3/2 and having the formula:

To 380 g of an aqueous solution containing 194 g of bisacrylamide (1 mole) there are added, over a one hour period, and between 10 and 15° C., 223 g of an aqueous solution containing 56.8 g (0.66 mole) of piperazine. The reaction medium is then left to stand for 24 hours at ambient temperature. The solution is cloudy and thickens. It is clarified by heating and is then poured slowly into 5 liters of acetone. The crosslinking agent precipitates. After filtration and drying, a white solid of which the dry extract is 80% is recovered.

EXAMPLE IIIb

Crosslinking, with the crosslinking agent prepared in Example IIIa, the polyamino-polyamide polymer obtained by condensation of adipic acid on diethylene triamine.

To 370 g of an aqueous solution containing 111 g (0.649 amine equivalent) of the polyamino-polyamide prepared according to Example A, there are added, at ambient temperature, 50 g of the crosslinking agent prepared in Example IIIa. The temperature of the reaction medium is then raised to 90° C. After 30 minutes the medium gels. The solution is rapidly adjusted to 10% dry extract by the addition thereto of 1050 g of water.

A clear, yellow green solution is obtained. The viscosity of this solution measured at 25° C. is equal to 58 centipoises.

EXAMPLE IVa

Bis-halohydrin oligomer crosslinking agent prepared from epichlorohydrin and piperazine in molar proportions of 5/4 and having the formula

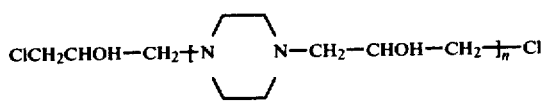

wherein n=4.

To 541 g of an aqueous solution containing 69.4 g (0.806 mole) of piperazine, there are added, over a 1 hour period, without exceeding 20° C., 92.5 g (1 mole) of epichlorohydrin. The reaction mixture is again maintained for 1 hour with agitation at 20° C.; then at the same temperature there are added 60 g (0.6 mole) of 40% NaOH over a 1 hour period.

EXAMPLE IVb

Crosslinking, with the crosslinking agent prepared in Example IVa, the polyamino-polyamide polymer obtained by the condensation of adipic acid on diethylene triamine.

To 787.5 g of an aqueous solution containing 157.5 g (0.92 amine milliequivalent) of the polyamino-polyamide prepared in Example A, there are added, at ambient temperature, 268 g of an aqueous solution containing 54.9 g of the crosslinking agent prepared in Example IVa. The temperature of the reaction medium is maintained for 4 h 50 min at 90° C. At this point, the reaction medium gels. By rapid addition of 1100 cc of water there is obtained a clear solution having 9.85% active material. The viscosity of this solution, measured at 25° C. is equal to 73 centipoises.

EXAMPLE Va

Preparation of a quaternized crosslinking agent having the formula

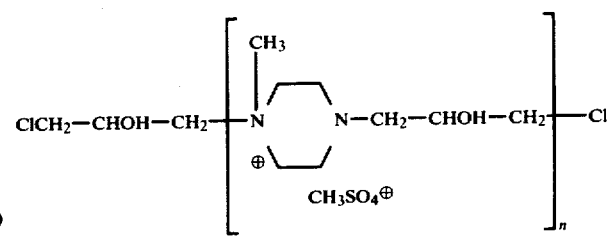

wherein n=4.

To 330 g of an aqueous solution containing 67.7 g (0.752 amine equivalent) of the croslinking agent prepared in Example IVa, there are added, over a 1 hour period and without exceeding 30° C., 47.4 g (0.376 mole) of dimethylsulfate.

The reaction medium is maintained with agitation for an additional 2 hours at this temperature.

EXAMPLE Vb

Crosslinking, with a crosslinking agent prepared in Example Va, the polyamino-polyamide polymer obtained by the condensation of adipic acid on diethylene triamine.

To 327.7 g of an aqueous solution containing 65.5 g (0.383 amine equivalent) of the polyamino-polyamide prepared in Example A, there are added, at ambient temperature, 155 g of an aqueous solution containing 47.25 g of the crosslinking agent prepared in Example Va. After 4 hours of heating at 85° C., the reaction mixture gels.

By rapid addition of 645 g of water, there is obtained a clear solution having 10% active material. The viscosity of this solution measured at 25° C. is 0.47 poise at 67.18 sec.$^{-1}$.

EXAMPLE VIa

Preparation of bis-azetidinium crosslinking agent of the formula

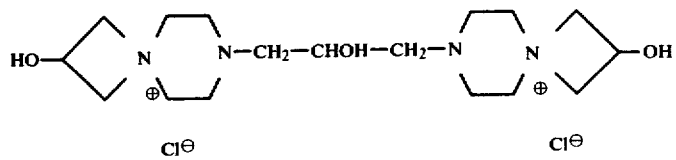

To 50 g (0.212 mole) of 1,3-bis piperazine-2-propanol, (prepared by the addition of epichlorohydrin to piperazine—as described in Example 15 of French application No. 74 42279 of Nov. 28, 1972, or in Example 15 of U.S. Patent 3,917,817) dissolved in 100 g of absolute ethyl alcohol, there are added at a temperature between 0° and 5° C., 43.5 g (0.47 mole) of epichlorohydrin. The reaction mixture is left to stand 24 hours at 0° C. The crosslinking agent is then precipitated from its solution in a large excess of ether. A white solid having a softening point of about 120° C. is isolated.

EXAMPLE VIb

Crosslinking, with a crosslinking agent, prepared in Example VIa, the polyamino-polyamide polymer obtained by the condensation of adipic acid on diethylene triamine.

To 386 g of an aqueous solution containing 77.2 g (0.452 amine equivalent) of the polyamino-polyamide prepared in Example A, there are added, at ambient temperature, 15.4 g (0.036 mole) of the crosslinking agent prepared in Example VIa. After 2 hr. 30 min. of heating at 90° C., the reaction medium gels. By rapid addition of 525 g of water, there is obtained a clear solution having 10% active material. The viscosity of this solution measured at 25° C. is 0.7 poise at 67.18 sec.$^{-1}$.

EXAMPLE VIIa

Preparation of bis-(chloracetyl)piperazine crosslinking agent of the formula:

This crosslinking agent is prepared by condensing 2 molecules of chloracetyl chloride on a molecule of piperazine in the presence of NaOH.

EXAMPLE VIIb

Crosslinking, with the crosslinking agent prepared in Example VIIa, the polyamino-polyamide polymer obtained by the condensation of adipic acid on diethylene triamine.

To 100 g of an aqueous solution containing 200 g (1.170 amine equivalents) of the polyamino-polyamide prepared in Example A, there are added, at ambient temperature, 24 g (0.1 mole) of bis-(chloracetyl)piperazine.

The temperature of the reaction medium is then raised to 90° C. After 30 minutes of heating the reaction medium gels. Then 1216 g of water are rapidly added and heating is continued at 80° C. for 1 hour. A clear solution is obtained having 10% active material. The viscosity of this solution measured at 25° C. is 0.29 poise at 88.41 sec.$^{-1}$.

EXAMPLE VIIIa

Preparation of bis-(1,1-bromo undecanoyl)piperazine crosslinking agent of the formula

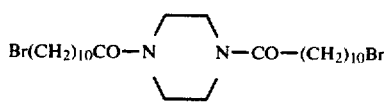

This crosslinking agent is prepared by the condensation of 2 molecules of bromoundecanoyl bromide and one molecule of piperazine in the presence of sodium hydroxide.

EXAMPLE VIIIb

Crosslinking, with the crosslinking agent prepared in Example VIIIa, the polyamino-polyamide polymer obtained by the condensation of adipic acid on diethylene triamine.

To 113.3 g of an aqueous solution containing 56.7 g (0.33 amine equivalent) of the polyamino-polyamide prepared in Example A, there are added, at ambient temperature, 60 g of an isopropanol solution containing 10 g (0.017 mole) of bis-(1,1-bromo undecanoyl) piperazine, prepared in Example VIIIa. The reaction medium is heated 2 hr. 30 min. at solvent reflux. The isopropanol is then distilled, while adding water until the attainment of a 10% aqueous solution of the resin (active material). The solution is slightly opalescent and its viscosity, measured at 25° C. is 0.052 poise at 87.93 sec.$^{-1}$.

EXAMPLE IXa

Preparation of an oligomer crosslinking agent of the formula

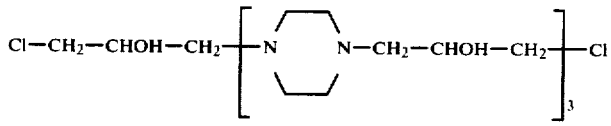

from epichlorohydrin and piperazine in molar proportions of 4/3.

To 1149 g of an aqueous solution containing 172 g (2 moles) of piperazine there are added, over a 1 hour period, 246.7 g (2.66 moles) of epichlorohydrin while maintaining the reaction mixture with agitation at 20° C.

After an additional hour of agitation at 20° C., there are added, at the same temperature and in the space of 1 hour, 133 g (1.33 mole) of 40% NaOH. A precipitation in the course of neutralization is observed. There are then added 638 g of water and the mixture is heated a few minutes at 50° C. to obtain a clear solution.

EXAMPLE IXb

Crosslinking, with the crosslinking agent prepared in Example IXa, the polyamino-polyamide polymer obtained by the condensation of adipic acid on diethylene diamine.

To 2000 g of an aqueous solution containing 400 g (2.34 amine equivalents) of the polyamino-polyamide prepared according to Example A, there are added 584 g of an aqueous solution containing 99.8 g of the crosslinking agent prepared in Example IXa. The reaction medium is then maintained with agitation at 90° C. for 5 hours. There are then added 2,414 g of water to obtain a clear solution having 10% active material. The viscosity of this solution measured at 25° C. is 0.22 poise.

EXAMPLE Xa

Preparation of an oligomer crosslinking agent of the formula:

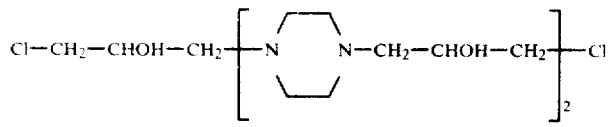

from epichlorohydrin and piperazine in molar proportions of 3/2.

To 1,221 g of an aqueous solution containing 172 g (2 moles) of piperazine there are added, over a 1 hour period and at 20° C., 277.5 g (3 moles) of epichlorohydrin while maintaining the reaction mixture under agitation and at 20° C. After an additional hour of agitation there are added, at a temperature of 20° C., 100 g (1 mole) of a 40% aqueous solution of NaOH.

On addition of 727.5 g of water and after a few minutes of heating, a clear solution of the said crosslinking agent is obtained.

EXAMPLE Xb

Crosslinking, with the crosslinking agent prepared in Example Xa, the polyamino-polyamide polymer obtained by the condensation of adipic acid on diethylene triamine.

To 2,000 g of an aqueous solution containing 400 g (2.34 amine equivalents) of the polyamino-polyamide prepared in accordance with Example A, there are added 472 g of an aqueous solution containing 83.8 g of the crosslinking agent prepared in Example Xa.

The reaction medium is maintained with agitation at 90° C. and after 4 hours of heating, the solution gels.

The solution is rapidly adjusted to 10% active material by the addition of 2,326 g of water.

A clear solution is obtained. The viscosity of this solution measured at 25° C. is 0.64 poise at 88.4 sec.$^{-1}$.

EXAMPLES OF USE

EXAMPLE 1a

A rinse composition is prepared by admixing the following components:

| | |
|---|---|
| Compound of Example VIb $$\left[ \begin{array}{c} CH_3 \\ | \\ -N^{\oplus}-(CH_2)_6-N^{\oplus}-CH_2-CHOH-CH_2- \\ | \\ CH_3 \\ Br^{\ominus} \end{array} \begin{array}{c} CH_3 \\ | \\ | \\ CH_3 \\ Br^{\ominus} \end{array} \right]$$ | 0.5 g active material 0.5 g active material |
| R—CHOH—CH$_2$—O—(—CH$_2$—CHOH—CH$_2$—O—)$_n$—H wherein R = C$_9$-C$_{10}$ alkyl and n has a statistical average value of 3.5 | 0.7 g |
| Phosphoric acid ester of ethoxylated oleyl alcohol sold under the name "DIVALIN SO" | 0.4 g |
| Water, sufficient for | 100 g |

The pH of this solution is 7-8. This rinse composition is applied to previously washed hair. The combing of the thus treated hair is excellent. The dry hair is particularly full, shiny and easy to style.

EXAMPLE 1b

A rinse composition is prepared by admixing the following components:

| | |
|---|---|
| Polymer obtained by the condensation of equimolar amounts of adipic acid and diethylene triamine and crosslinked with 0.11 mole of epichlorohydrin per amine group (according to Example 1a of S.N. 762,804) | 0.5 g active material |
| Compound of Example VIIIb | 0.5 g active material |
| R—CHOH—CH$_2$—O—(—CH$_2$—CHOH—CH$_2$—O—)$_n$—H wherein R = C$_9$-C$_{10}$ alkyl and n has a statistical average value of 3.5 | 0.7 g |
| Phosphoric acid ester of ethoxylated oleyl alcohol sold under the mark "DIVALIN SO" | 0.4 g |
| Water, sufficient for | 100 cc |

The pH of this solution is 7-8. This rinse composition is applied to previously washed hair. The combing of the thus treated hair is excellent. The dry hair is particularly full, shiny and easy to style.

EXAMPLE 1c

An emulsion having the following composition is prepared:

| | |
|---|---|
| Petrolatum oil | 15 g |
| Cetyl-stearyl alcohol, partially sulfated, sold under the mark "Cire de lanette" | 2.5 g |
| Cetyl stearyl alcohol polyoxyethylenated with 10 moles of ethylene oxide, sold under the name "SIMULSOL 1951 RD" | 2.5 g |

| Compound of Example VIIb | 0.7 g |
| Water, sufficient for | 100 g |

The pH of this solution is 9.5. Its application, followed by rinsing off this "rinse" in the form of an emulsion on the hair, facilitates its untangling; imparts to it softness; and gives good liveliness to the hair style.

EXAMPLE 1d

An emulsion having the following composition is prepared:

| Petrolatum oil | 15 g |
| Cetyl stearyl alcohol, partially sulfated, sold under the mark "Cire de lanette" | 2.5 g |
| Cetyl stearyl alcohol polyoxyethylated with 10 moles of ethylene oxide, sold under the name "SIMULSOL 1951 RD" | 2.5 g |
| Compound of Example IIIb | 0.5 |
| Water, sufficient for | 100 g |

The pH of this solution is 9. This "rinse" is applied to the hair, and left in contact therewith for a few minutes. It is then rinsed off. The untangling of the hair is facilitated; the hair has a firmer touch; and the liveliness of the hair style is improved.

EXAMPLE 2a

A hair setting lotion is prepared by admixing the following components:

$$\left[ \begin{array}{cc} \overset{CH_3}{\underset{CH_3}{\overset{|}{N^{\oplus}}}}-(CH_2)_6-\overset{CH_3}{\underset{CH_3}{\overset{|}{N^{\oplus}}}}-CH_2-CHOH-CH_2 \\ Br^{\ominus} \quad\quad Br^{\ominus} \end{array} \right]$$

0.5 g active material

| Compound of Example VIb | 0.5 g active material |
| Quaternary vinylpyrrolidone copolymer having a molecular weight of about 100,000, sold under the name "GAFQUAT 734" | 0.4 g active material |
| Perfume | 0.2 g |
| Dyes | 0.05 g |
| Water, sufficient for | 100 cc |

The pH of this lotion is 7.3. When applied to dyed hair, this hair setting lotion facilitates the combing of wet hair. The dry hair is soft and easy to style. This effect of softness lasts after several shampooings.

EXAMPLE 2b

The following hair setting composition is prepared:

| Compound of Example Ib | 0.5 g active material |
| Quaternary vinylpyrrolidone copolymer having a molecular weight of about 100,000, sold under the name "GAFQUAT 734" | 0.4 g active material |
| Perfume | 0.1 g |
| Dyes | 0.1 g |
| Water, sufficient for | 100 cc |

The pH of this composition is 7.3. When applied to dyed hair, this hair setting lotion facilitates the combing of wet hair. The dry hair is soft and easy to style. This effect of softness lasts after several shampooings.

EXAMPLE 2c

The following hair setting lotion is prepared:

| Compound of Example IIb | 0.6 g active material |
| Quaternary vinylpyrrolidone copolymer having a molecular weight of about 100,000 and sold under the name "Gafquat 734" | 0.5 g |
| Quaternized cellulose sold under the name "JR 400" | 0.3 g |
| Ethyl alcohol, sufficient for | 15° |
| Perfume | 0.1 g |
| Water, sufficient for | 100 cc |
| pH, adjusted to 8. | |

When applied to washed hair, this hair setting lotion facilitates combing. After drying and setting the hair, the hair is soft, shiny and is easy to style. This effect lasts after several shampooings.

EXAMPLE 2d

The following hair setting lotion is prepared:

| Compound of Example IVb | 0.3 g active material |
| Quaternary vinylpyrrolidone copolymer having a molecular weight of about 100,000 and sold under the name "Gafquat 734" | 0.5 g |
| Quaternized cellulose, sold under the name "JR 400" | 0.3 g |
| Ethyl alcohol, sufficient for | 15° |
| Perfume | 0.1 g |
| Water, sufficient for | 100 cc |
| pH, adjusted to 8 | |

When applied to washed hair, this setting lotion facilitates combing. After drying and setting, the hair is soft, shiny and easy to style. This effect lasts after several shampooings.

EXAMPLE 3a

The following "brushing lotion" is prepared:

| | | |
|---|---|---|
| Compound of Example Vb | 0.6 | g active material |
| Ethanol, sufficient for | 10° | |
| Dyes | 0.1 | g |
| Perfume | 0.1 | g |
| Water, sufficient for | 100 | g |

The pH of this solution is adjusted to 7.

EXAMPLE 3b

The following "brushing lotion" is prepared:

| | | |
|---|---|---|
| Compound of Example IIIb | 0.4 | g active material |
| Ethanol, sufficient for | 10° | |
| Dyes | 0.1 | g |
| Perfume | 0.1 | g |
| Water, sufficient for | 100 | cc |

The pH of this solution is adjusted to 8.

EXAMPLE 3c

The following "brushing lotion" is prepared:

| | | |
|---|---|---|
| Compound of Example VIIIb | 0.5 | g active material |
| Ethanol, sufficient for | 20° | |
| Dyes | 0.2 | g |
| Perfume | 0.1 | g |
| Water, sufficient for | 100 | cc |

The pH of this solution is adjusted to 6.

EXAMPLE 3d

The following "brushing lotion" is prepared:

| | | |
|---|---|---|
| Compound of Example Ib | 0.5 g | active material |
| Dyes | 0.1 g | |
| Perfume | 0.1 g | |
| Water, sufficient for | 100 cc | |

EXAMPLE 3e

The following "brushing lotion" is prepared:

| | | |
|---|---|---|
| Compound of Example IIb | 0.8 | g active material |
| Ethanol, sufficient for | 40° | |
| Dyes | 0.05 | g |
| Perfume | 0.1 | g |
| Water, sufficient for | 100 | cc |

The pH of this solution is adjusted to 7.

EXAMPLE 3f

The following "brushing lotion" is prepared:

| | | |
|---|---|---|
| Compound of Example VIIb | 0.6 g | active material |
| Dyes | 0.05 g | |
| Perfume | 0.15 g | |
| Water, sufficient for | 100 cc | |

The pH of this solution is adjusted to 6.

The "brushing lotions" of Examples 3a–3f are applied to wet or dry hair after shampooing. The hair is styled using a brush, all while drying the hair with the aid of a hand dryer. Very good passage of the brush through the hair is noted as is a prolonged holding of the style. The hair thus treated is shiny and soft.

EXAMPLE 4a

The following shampoo composition is prepared:

| | |
|---|---|
| Triethanolamine $C_{12}$–$C_{14}$ alkyl sulfate | 5 g |
| $R-CHOH-CH_2-O-(-CH_2-CHOH-CH_2-O-)_n-H$ wherein R is $C_9$ to $C_{12}$ alkyl and n has a statistical average value of 3.5 | 5 g |
| Lauric diethanolamide | 3 g |
| Compound of Example VIb | 1 g |
| Perfume | 0.1 g |
| Dyes | 0.01 g |
| Water, sufficient for | 100 g | pH adjusted to 8 with triethanolamine.

This shampoo composition is provided in the form of a clear liquid. It facilitates combing wet hair and it imparts control and body to the hair.

EXAMPLE 4b

The following shampoo composition is prepared:

| | |
|---|---|
| $R-CHOH-CH_2-O-(-CH_2-CHOH-CH_2-O-)_n-H$ wherein R is $C_9$ to $C_{12}$ alkyl and n has a statistical average value of 3.5 | 10 g |
| Copra diethanolamide | 3 g |
| Compound of Example IIIb | 1 g active material |
| Water, sufficient for | 100 g |

The pH of this composition initially was 8.7 and it was then adjusted to 6 using lactic acid.

When applied to natural hair, this shampoo composition, provided in the form of a clear liquid, facilitates combing wet hair. The dry hair is full and lively.

EXAMPLE 4c

The following shampoo composition is prepared:

| | |
|---|---|
| Ammonium lauryl sulfate | 25 g |
| Diethanolamide of the fatty acids of copra | 2 g |
| Compound of Example VIIIb | 1 g active material |
| Water, sufficient for | 100 g |

Initial pH of 8.1 adjusted to 7.7 with lactic acid.

When applied to dyed, permanent waved hair, this slightly opalescent clear shampoo composition produces convenient untangling of wet hair. After drying the hair is full and lively.

EXAMPLE 4d

The following shampoo composition is prepared:

| | |
|---|---|
| Lauryl alcohol polyoxyethylenated with 12 moles of ethylene oxide | 5 g |
| $C_{12}$-$C_{18}$ alkyl dimethyl carboxymethyl ammonium hydroxide, sold under the name "DEHYTON AB 30" | 10 g |
| Lauric diethanolamide | 3 g |
| Compound of Example Ib | 0.8 g active material |
| Water, sufficient for | 100 g |

The initial pH of 7.8 was adjusted to 6 with lactic acid.

When applied to dyed hair, this shampoo composition, provided in the form of a slightly opalescent clear liquid, facilitates the combing of wet hair and makes it softer. The dry hair is lively, full and controlled.

EXAMPLE 4e

The following shampoo composition is prepared:

| | |
|---|---|
| $C_{12}$-$C_{14}$ alkyl sulfate | 12.5 g |
| Lauric diethanolamide | 2 g |
| Compound of example IIb | 0.7 active material |
| Water, sufficient for pH = 7.4 | 100 g |

When applied to natural hair, this clear liquid shampoo composition provides good untangling of wet hair. The dry hair is full, lively and controlled.

EXAMPLE 4f

The following shampoo composition is prepared:

| | |
|---|---|
| $C_{12}$-$C_{14}$ alcohol ethoxylated with 10 moles of ethylene oxide and carboxymethylated, sold under the mark "AKYPO RLM 100" | 3.5 g |
| Lauryl alcohol polyethoxylated with 12 moles of ethylene oxide | 10 g |
| Compound of Example IIB | 0.6 g active material |
| Homopolymer of dimethyl diallyl ammonium chloride, M.W. = about 100,000, sold under the mark "MERQUAT 100" | 0.4 g active material |
| Water, sufficient for pH = 7.4 | 100 g |

When applied to dyed hair, this liquid shampoo composition improves the untangling of wet hair. The dry hair is controlled and shiny.

EXAMPLE 4g

A shampoo composition having the same formulation as that in Example 4f is prepared except that the 0.6 g of the compound of Example IIb is replaced by 0.5 g of the compound of Example VIIIb.

The properties of this shampoo composition are similar to those of the shampoo composition of Example 4f.

EXAMPLE 4h

The following shampoo composition is prepared:

| | |
|---|---|
| $C_{12}$-$C_{14}$ alcohol ethoxylated with 10 moles of ethylene oxide and carboxymethylated, sold under the mark "AKYPO RLM 100" | 3.5 g |
| Lauryl alcohol polyethoxylated with 12 moles of ethylene oxide | 10 g |
| Compound of Example Ib | 0.6 g active material |
| Homopolymer of dimethyl diallyl ammonium chloride, M. W. = about 100,000, sold under the mark "MERQUAT 100" | 0.4 g active material |
| Perfume | 0.15 g |
| Dyes | 0.02 g |
| Water, sufficient for pH, adjusted to 7 | 100 g |

When applied to dyed hair, this shampoo composition provides good untangling of wet hair and imparts to dry hair liveliness and fullness.

EXAMPLE 4i

The following shampoo composition is prepared:

| | |
|---|---|
| Hydroxy propyl methyl cellulose | 0.2 g |
| Diethanolamide of the fatty acids of copra | 3 g |
| Triethanolamine $C_{12}$-$C_{14}$ alkyl sulfate | 10 g |
| Compound of Example VIIb | 0.8 g active material |
| Perfume | 0.15 g |
| Dyes | 0.01 g |
| Water, sufficient for pH, adjusted to 7.8 | 100 g |

When applied to natural permanent waved hair, this shampoo composition provides good untangling of wet hair and imparts to dry hair liveliness and fullness.

EXAMPLE 4j

The following shampoo composition is prepared:

| | |
|---|---|
| Lauryl alcohol polyethoxylated with 12 moles of ethylene oxide | 7 g |
| R—CHOH—CH$_2$—O$-$($-$CH$_2$—CHOH—CH$_2$—O$\displaystyle)_{\overline{n}}$H wherein R = C$_9$ to C$_{12}$ alkyl and n has a statistical average value of 3.5 | 7 g |
| Diethanolamide of copra fatty acids | 2 g |
| Compound of Example IVb | 0.8 g active material |
| Perfume | 0.1 g |
| Dyes | 0.01 g |
| Water, sufficient for pH, adjusted to 7.2 | 100 g |

When applied to dyed hair, this shampoo composition provides good untangling of wet hair and imparts to dry hair liveliness and fullness.

EXAMPLE 4k

The following shampoo composition is prepared:

| | | |
|---|---|---|
| R—CHOH—CH$_2$—O—(CH$_2$—CHOH—CH$_2$—O$)_n$—H wherein R = C$_9$ to C$_{12}$ alkyl and n has a statistical average value of 3.5 | 10 g | |
| Diethanolamide of copra fatty acids | 3 g | |
| Compound of Example IIb | 0.5 g | active material |
| 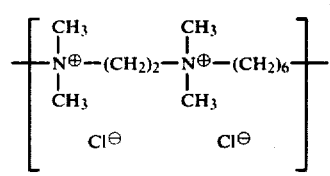 | 0.2 g | active material |
| Water, sufficient for | 100 g | | pH, initially 8.6; adjusted to 6 with lactic acid

When applied to natural hair, this shampoo composition in the form of a clear liquid, facilitates untangling of wet hair. Dry hair, thus treated, is controlled and shiny.

EXAMPLE 4l

The following shampoo composition is prepared:

| | |
|---|---|
| R—CHOH—CH$_2$—O—(CH$_2$—CHOH—CH$_2$—O$)_n$—H wherein R = C$_9$ to C$_{12}$ alkyl and n has a statistical average value of 3.5 | 10 g |
| Triethanolamine C$_{12}$–C$_{14}$ alkyl sulfate | 2 g |
| Diethanolamide of copra fatty acids | 3 g |
| Compound of Example Ib | 0.5 g active material |
| 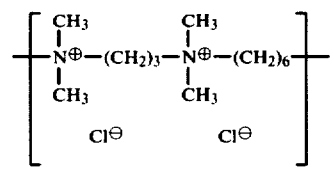 | 0.1 g active material |
| Water, sufficient for | 100 g | pH, initially—7.9; adjusted to 6 with lactic acid

When applied to dyed hair, this shampoo composition in the form of a slightly opalescent liquid facilitates the untangling of wet hair and imparts softness thereto. Dry hair, thus treated, is lively and full.

EXAMPLE 4m

The following shampoo composition is prepared:

| | | |
|---|---|---|
| C$_{12}$–C$_{14}$ alcohol ethoxylated with 10 moles of ethylene oxide and carboxymethylated, sold under the mark "AKYPO RLM 100" | 3 g | |
| Lauryl alcohol polyethoxylated with 12 moles of ethylene oxide | 7 g | |
| Lauric diethanolamide | 3 g | |
| Compound of Example IIIb | 0.6 g | active material |
| 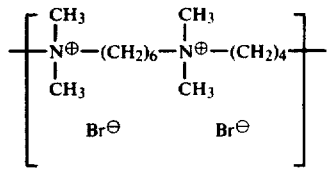 | 0.3 g | active material |
| Water, sufficient for | 100 g | | pH, initially—4.5; adjusted to 7.2 with triethanolamine

When applied to dyed hair, this shampoo composition in the form of a clear liquid, facilitates the untangling of wet hair. Dry hair, thus treated, is shiny.

EXAMPLE 4n

The following shampoo composition is prepared:

| | | |
|---|---|---|
| R—CHOH—CH$_2$—O—(CH$_2$—CHOH—CH$_2$—O$)_n$—H wherein R = C$_9$ to C$_{12}$ alkyl and n has a statistical average value of 3.5 | 10 g | |
| Diethanolamine of copra fatty acids | 2 g | |
| Compound of Example Ib | 0.7 g | active materials |
| 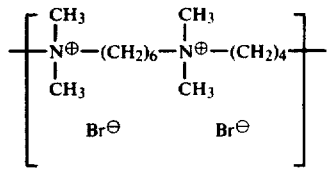 | 0.3 g | |
| Water, sufficient for | 100 g | | pH = 7

When applied to natural, permanent waved hair, this shampoo composition in the form of a clear liquid, facilitates the untangling of wet hair and imparts softness thereto. Dry hair, thus treated, is lively, full and easy to control.

EXAMPLE 4o

The following shampoo composition is prepared:

| | |
|---|---|
| Triethanolamine C$_{12}$–C$_{14}$ alkyl sulfate | 10 g |
| Lauric diethanolamide | 2 g |
| Hydroxypropylmethyl cellulose | 0.2 g |
| Compound of Example Vb | 0.8 g |
| Perfume | 0.1 g |
| Dyes | 0.01 g |
| Water, sufficient for | 100 g | pH, adjusted to 8 with triethanolamine

This clear liquid shampoo composition improves the untangling of wet hair. It imparts to dry hair thus treated good control.

EXAMPLE 4p

The following shampoo composition is prepared:

| | |
|---|---|
| Triethanolamine $C_{12}$–$C_{14}$ alkyl sulfate | 15 g |
| Hydroxypropylmethyl cellulose | 0.2 g |
| Lauric diethanolamide | 3 g |
| Compound of Example IXb | 1 g |
| Perfume | 0.2 g |
| Dyes | 0.01 g |
| Water, sufficient for | 100 g | pH = 7.7

EXAMPLE 4q

The following shampoo composition is prepared:

| | |
|---|---|
| Triethanolamine $C_{12}$–$C_{14}$ alkyl sulfate | 10 g |
| Hydroxypropylmethyl cellulose | 0.3 g |
| Compound of Example Xb | 1 g |
| Perfume | 0.1 g |
| Dyes | 0.015 g |
| Water, sufficient for | 100 g | pH = 7.7

EXAMPLE 5a

The following "after-shampoo" care cream is prepared:

| | |
|---|---|
| Cetyl alcohol | 20 g |
| Cetyl alcohol oxyethylenated with 10 moles of ethylene oxide, sold under the mark "BRIJ 50" | 12 g |
| $\left[ \begin{array}{cc} CH_3 & CH_3 \\ \| & \| \\ -N^{\oplus}-(CH_2)_3-N^{\oplus}-(CH_2)_6- \\ \| & \| \\ CH_3 & CH_3 \\ Cl^{\ominus} & Cl^{\ominus} \end{array} \right]$ | 1.5 g active material |
| Compound of Example VIIb | 0.5 g active material |
| Phosphoric acid ester of ethoxylated oleyl alcohol, sold under the mark "DIVALIN SO" | 1 g |
| Water, sufficient for | 100 g |

EXAMPLE 5b

The following "after-shampoo" care cream is prepared:

| | |
|---|---|
| Cetyl alcohol | 22 g |
| Cetyl alcohol oxyethylenated with 10 moles of ethylene oxide, sold under the mark "BRIJ 56" | 10 g |
| Compound of Example IVb | 0.5 g active material |
| Phosphoric acid ester of ethoxylated oleyl alcohol, sold under the mark "DIVALIN SO" | 1.2 g |
| Water, sufficient for | 100 g |

The care creams of Examples 5a and 5b are applied to clean, moist or dried hair, in an amount sufficient to impregnate and cover the hair (about 60 to 80 g). The cream is permitted to remain in contact with the hair for 30–40 minutes at which time it is then rinsed off. The wet hair is very soft and easy to comb. The hair is then set and dried under a hood. The dry hair combs easily and has a silky touch; is shiny and lively; has body and is full.

EXAMPLE 5c

The following "before shampoo" care cream is prepared:

| | |
|---|---|
| Stearic acid | 12 g |
| Cetyl-stearyl alcohol oxyethylenated with 10 moles of ethylene oxide | 4 g |
| Monoethanolamine | 2 g |
| Glycerine | 4 g |
| $\left[ \begin{array}{cc} CH_3 & CH_3 \\ \| & \| \\ -N^{\oplus}-(CH_2)_3-N^{\oplus}-(CH_2)_6- \\ \| & \| \\ CH_3 & CH_3 \\ Cl^{\ominus} & Cl^{\ominus} \end{array} \right]$ | 1.2 g active material |
| Compound of Example VIIIb | 0.5 g active material |
| Perfume and dyes | |
| Water, sufficient for | 100 g | pH, adjusted to 7

EXAMPLE 5d

The following "before shampoo" care cream is prepared:

| | |
|---|---|
| Stearic acid | 12 g |
| Cetyl-stearyl alcohol oxyethylenated with 10 moles of ethylene oxide | 6 g |
| Monoethanolamine | 3 g |
| Glycerine | 3 g |
| Compound of Example IIIb | 0.8 g active material |
| Perfume - Dyes | |
| Water, sufficient for | 100 g | pH, adjusted to 7

The care creams of Example 5c and 5d are applied to soiled, wet hair at a rate of 60 grams. The hair is impregnated therewith by rubbing and the cream is permitted to remain in contact therewith for 30 minutes. The hair is then shampooed. The wet hair is very soft and easy to untangle. After setting and drying, the hair has a particularly soft feel; it is shiny, lively and has body. This effect lasts after several shampooings.

EXAMPLE 6a

The following hair structuring lotion without rinsing is prepared:

| | |
|---|---|
| Dimethylol ethylene thiourea of the formula | |

-continued

|  |  |
|---|---|
| $\begin{array}{c} \text{CH}_2\text{OH} \\ \text{CH}_2-\text{N} \\ \phantom{\text{CH}_2-\text{N}}\text{C}=\text{S} \\ \text{CH}_2-\text{N} \\ \phantom{\text{CH}_2-\text{N}}\text{CH}_2\text{OH} \end{array}$ | 0.5 g |
| Quarternary vinylpyrrolidone copolymer, M.W. = about 1,000,000, sold under the mark "GAFQUAT 755" | 0.5 g |
| Compound of Example Ib | 0.4 g active material |
| Vinylpyrrolidone-vinyl acetate copolymer, VP/VA = 70:30 | 0.8 g |
| Phosphoric acid, sufficient for | pH = 3 |
| Water, sufficient for | 100 cc |

This lotion is applied to washed and dried hair after a shampoo and before setting. In the wet state the hair untangles easily and has a silky touch. After setting and drying, the hair is shiny and lively.

EXAMPLE 6b

This example is similar to Example 6a except that the compound of Example Ib is replaced by an equal amount of the compound of Example IVb.

EXAMPLE 7a

The following non-rinse lotion for use before a permanent is prepared:

| | |
|---|---|
| Trimethyl cetylammonium bromide | 0.1 g |
| Compound of Example IVb | 1.5 g |
| Perfume | 0.1 g |
| Dyes | 0.1 g |
| Citric acid, sufficient for | pH = 5 |
| Water, sufficient for | 100 g |

When applied to washed hair, this non-rinse product facilitates combing and permits easy implementation of the permanent wave. It protects the hair and prolongs the hold of the waves.

EXAMPLE 7b

The following non-rinse lotion for use before a permanent is prepared:

| | |
|---|---|
| Trimethylcetylammonium bromide | 0.15 g |
| Compound of Example VIIb | 2.2 g |
| Perfume | 0.2 g |
| Dyes | 0.01 g |
| Citric acid, sufficient for | pH = 4 |
| Water, sufficient for | 100 g |

When applied to washed hair, this non-rinse product facilitates combing and permits easy implementation of the permanent. It protects the hair and prolongs the hold of the wave.

EXAMPLE 8a

The following permanent wave composition is prepared:

| Reducing agent liquid | |
|---|---|
| Thioglycolic acid | 3 g |
| Thiolactic acid | 2 g |
| Ammonia, 22° Be | 4 g |
| Triethanolamine | 3.5 g |
| Compound of Example VIb | 1.4 g |
| Perfume | 0.2 g |
| Dyes | 0.05 g |
| Water, sufficient for | 100 g |

| Fixing Agent Liquid | |
|---|---|
| Potassium bromate | 9.5 g |
| Cetylpyridinium chloride | 1 g |
| Tartaric acid, sufficient for | pH = 6.5 |
| Perfume | 0.1 g |
| Dyes | 0.05 g |
| Water, sufficient for | 100 g |

On sensitized hair, the reducing agent liquid is applied very easily and it deeply penetrates the hair. After rinsing and after application of the fixing agent liquid, a very strong and regular wave is attained. The hair is in a very beautiful cosmetic state. After drying, the hair is very soft and particularly shiny. The hold of the hair style is particularly good.

EXAMPLE 8b

The following permanent wave composition is prepared:

| Reducing Agent Liquid | |
|---|---|
| Thioglycolic acid | 3.5 g |
| Thiolactic acid | 2 g |
| Ammonia, 22° Be | 3.5 g |
| Triethanolamine | 4 g |
| Compound of Example VIIIb | 2 g |
| Perfume | 0.2 g |
| Dyes | 0.01 g |
| Water, sufficient for | 100 g |

| Fixing Agent Liquid | |
|---|---|
| Potassium bromate | 8 g |
| Cetylpyridinium chloride | 0.8 g |
| Tartaric acid, sufficient for | pH = 6.5 |
| Perfume | 0.2 g |
| Dyes | 0.05 g |
| Water, sufficient for | 100 g |

On sensitized hair, the reducing agent liquid is applied easily and it penetrates deeply into the hair. After rinsing and after application of the fixing agent liquid, a very strong and very regular wave is obtained. The hair is in a very beautiful cosmetic state. After drying, the hair is very soft and particularly shiny. The hold of the hair style is particularly good.

What is claimed is:

1. A cosmetic composition for the hair comprising an aqueous or hydroalcoholic solution of 0.1–5 percent by weight of said composition of at least one water soluble crosslinked polymer selected from the group consisting of a crosslinked polymer obtained by crosslinking a polyamino-polyamide with a crosslinking agent, said polyamino-polyamide being prepared by the polycondensation of (a) an acidic compound selected from the group consisting of (i) an organic dicarboxylic acid, (ii) ethylenically unsaturated aliphatic mono- or di-carboxylic acid, (iii) ester of said acids of (i) and (ii), and (iv) mixtures of (i), (ii) and (iii) on (b) a polyamine selected from the group consisting of bis-primary and mono- or bis-secondary polyalkylene polyamines, said polyamine (b) being replaceable by a member selected from the group consisting of (1) 0–20 mole percent hexamethylene diamine, (2) 0–40 mole percent bis-primary amine and (3) 0-40 mole percent bis-secondary amine, said crosslinking agent being selected from the group consisting of:

(I) simple bi-functional compounds selected from the group consisting of (1) bis-halohydrins resulting from the reaction of an epihalohydrin with a primary amine, a bis-secondary diamine, a bis-phenol or a bis-mercaptan, (2) a bis-azetidinium, (3) a bis-haloacyl diamine, and (4) an alkyl bis-halide of the formula

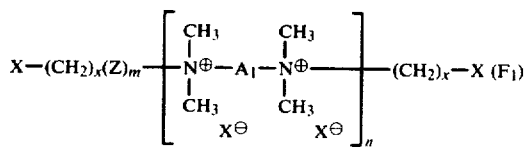

wherein X=Cl or Br, Z represents

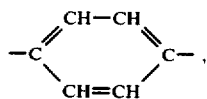

$x = 1$ to 3, $m = 0$ or 1, $n = 0$ or 1, $m$ and $n$ not representing 1 at the same time, with the proviso that when $m = 1$, $x = 1$, $A_1$ represents a saturated divalent hydrocarbon radical having 2, 3, 4 or 6 carbon atoms or 2-hydroxy propylene;

(II) an oligomer obtained by the reaction of compound (a) selected from the group consisting of compounds (1), (2), (3) and (4), each defined above, (5) an epihalohydrin, (6) a bis-epoxide and (7) a bis-unsaturated derivative, with a compound (b) which is a bi-functional compound reactive with said compound (a), said compound (b) being selected from the group consisting of a primary amine, a bis-secondary diamine, a bis-mercaptan and a bis-phenol, the molar ratio of (b):(a) being between 0.1 and 0.9;

(II-bis) an oligomer obtained by the reaction of compound ($a_1$) selected from the group consisting of compounds (1), (3), (4) and (6) each defined above, with a bis-tertiary diamine ($b_1$) which is a bi-functional compound reactive with said compound ($a_1$), the molar ratio of ($b_1$):($a_1$) being between 0.1 and 0.9;

(III) the quaternization product of compound ($a_2$) selected from the group consisting of (1) a bis-halohydrin resulting from the reaction of an epihalohydrin with piperazine, a bis-phenol or a bis-mercaptan, (2) a bis-azetidinium, (3) a bis-haloacyl diamine, (4) an alkyl bis-halide of formula $F_1$ above, (6) a bis-epoxide, (7) a bis-unsaturated derivative, (8) an oligomer II obtained by the reaction of a compound ($a_3$) selected from the group consisting of compounds (1), (2), (3), (4), (6), and (7) each defined above with a compound ($b_3$) which is a bi-functional compound reactive with said compound ($a_3$), said compound ($b_3$) being selected from the group consisting of a primary amine, a bis-secondary diamine, a bis-mercaptan and a bis-phenol, the molar ratio of ($b_3$):($a_3$) being between 0.1 and 0.9, (9) an oligomer obtained by the reaction of an epihalohydrin ($a_4$) with a compound ($b_4$) which is a bi-functional compound reactive with said compound ($a_4$), said compound ($b_4$) being selected from the group consisting of piperazine, a bis-mercaptan, a bis-phenol and a bis-epoxide of piperazine, the molar ratio of ($b_4$):($a_4$) being between 0.1 and 0.9, and (10) an oligomer obtained by the reaction of a compound ($a_5$) selected from the group consisting of (1) a bis-halohydrin resulting from the reaction of an epihalohydrin with piperazine, a bis-phenol or a bis-mercaptan, (2) a bis-haloacyl diamine, (3) an alkyl bis-halide of formula $F_1$ above and (4) a bis-epoxide, with a compound ($b_5$), said compound ($b_5$) being a bis-tertiary diamine, the molar ratio ($b_5$):($a_5$) being between 0.1 and 0.9;

said product having a tertiary amine group alkylated with an alkylating agent (c) selected from the group consisting of methyl or ethyl chloride, bromide, iodide, sulfate, mesylate and tosylate, benzyl chloride or bromide, ethylene oxide, propylene oxide and glycidol;

said crosslinking agent being employed in an amount of 0.025 to 0.35 mole per amine group of said polyamino-polyamide, said crosslinked polymer in said composition being perfectly soluble in a 10 weight percent solution thereof in water without gel formation, said 10 weight percent solution having a viscosity at 25° C. greater than 3 centipoises and said crosslinked polymer being characterized by having no reactive group, having no alkylating property and being chemically stable.

2. The cosmetic composition of claim 1 wherein said acidic compound employed in preparing said polyamino-polyamide is selected from the group consisting of adipic acid, terephthalic acid, esters of said acids and the addition product of ethylene diamine on acrylic acid, methacrylic acid or itaconic acid, or their esters.

3. The cosmetic composition of claim 1 wherein the polyamide employed in preparing said polyamino-polyamide is selected from the group consisting of diethylene triamine, dipropylene triamine, triethylene tetramine and a mixture of any one thereof with one or more of ethylene diamine, hexamethylene diamine and piperazine.

4. The cosmetic composition of claim 1 wherein said polyamino-polyamide is obtained by the condensation of adipic acid on diethylene triamine.

5. The cosmetic composition of claim 1 wherein said crosslinking agent is employed in an amount of 0.025 to about 0.2 mole per amine group of said polyamino-polyamide.

6. The cosmetic composition of claim 1 wherein said crosslinking agent is employed in an amount of 0.025 to about 0.1 mole per amine group of said polyamino-polyamide.

7. The cosmetic composition of claim 1 wherein the bi-functional reactive compound (b) in crosslinking agent (II) is selected from the group consisting of a primary amine, a bis-secondary amine and a bis-mercaptan.

8. The cosmetic composition of claim 1 wherein the bi-functional reactive compound (b) in crosslinking agent (II) is selected from the group consisting of piperazine and 1,2-dithiol ethane.

9. The cosmetic composition of claim 1 wherein compound (a) in crosslinking agent (II) is selected from the group consisting of (1) a bis-halohydrin resulting from the reaction of an epihalohydrin with a primary amine, a bis-secondary amine, a bis-phenol or a bis-mercaptan, (2) a bis-azetidinium, (3) a bis-haloacyl diamine, (4) an alkyl bis-halide of the formula $$X-(CH_2)_x(Z)_m\left[\begin{array}{c}CH_3\\|\\N^\oplus-A_1-N^\oplus\\|\\CH_3\\X^\ominus\end{array}\begin{array}{c}CH_3\\|\\\\|\\CH_3\\X^\ominus\end{array}\right]_n(CH_2)_x-X$$

wherein X=Cl or Br, Z represents $$-C\begin{array}{c}CH-CH\\\\\\CH=CH\end{array}C-,$$

x=1–3, m=0 or 1, n=0 or 1, m and n not representing 1 at the same time, when n=1, x=1, and $A_1$ represents a saturated divalent hydrocarbon radical having 2, 3, 4 or 6 carbon atoms or 2-hydroxy propylene, (5) an epihalohydrin, and (6) a bis-epoxide and
the compound (b) is a bis-phenol.

10. The cosmetic composition of claim 9 wherein compound (b) is bis-phenol A or 2,2-(4,4′-dihydroxy diphenyl) propane.

11. The cosmetic composition of claim 1 wherein the bi-functional reactive compound ($b_1$) in crosslinking agent (II-bis) is a bis-tertiary diamine.

12. The cosmetic composition of claim 1 wherein compound ($b_1$) is selected from the group consisting of N,N,N′,N′-tetramethyl ethylene-, propylene-, butylene- or hexamethylene-diamine.

13. The cosmetic composition of claim 1 wherein the alkylating agent (c) is dimethyl sulfate.

14. The cosmetic compositon of claim 1 wherein said bis-azetidinium is derived from a bis-halohydrin wherein the halohydrin units are linked to the remainder of the molecule by tertiary nitrogen groups, said bis-azetidinium carrying two azetidinium groups or one azetidinium group and one halohydrin group.

15. The cosmetic composition of claim 1 wherein said crosslinking agent is selected from the group consisting of
a bis halohydrin selected from the group consisting of $$X-CH_2-CH-CH_2\left[\!\!-N\diagdown\!\!\diagup N-CH_2-CH-CH_2\!\!-\right]_n X, \quad (1)$$
$$\phantom{X-CH_2-}OH\phantom{xxxxxxxxxxxxxxxxxx}OH$$

wherein n=1–4, $$X-CH_2-CHOH-CH_2-N\diagdown\!\!\diagup N-CH_2-CHOH-CH_2-N\diagdown\!\!\diagup N-CH_2-CHOH-CH_2-X \quad (2)$$

$$X-CH_2-CHOH-CH_2-N-(CH_2)_n-N-CH_2-CHOH-CH_2-X, \quad (3)$$
$$\phantom{X-CH_2-CHOH-CH_2-}|\phantom{-(CH_2)_n-}|$$
$$\phantom{X-CH_2-CHOH-CH_2-}CH_3\phantom{-(CH_2)_n-}CH_3$$

wherein n=2–6, $$X-CH_2-CHOH-CH_2-N-CH_2-CHOH-CH_2X, \quad \text{wherein } R=C_nH_{2n+1} \quad (4)$$
$$\phantom{X-CH_2-CHOH-CH_2-}|$$
$$\phantom{X-CH_2-CHOH-CH_2-}R$$

wherein n = 1–18 or —$(CH_2-CH_2-O)_mH$ wherein m = 1 or 2, $$X-CH_2-CHOH-CH_2-O-\!\!\left[\!-CH_2-CH_2-O-\right]_p\!\!-CH_2-CHOH-CH_2X \quad (5)$$

wherein p = 0–25, $$X-CH_2-CHOH-CH_2-O-\!\!\left\langle\!\!\!\begin{array}{c}\phantom{x}\end{array}\!\!\!\right\rangle\!\!-\!\!\underset{\underset{CH_3}{|}}{\overset{\overset{CH_3}{|}}{C}}\!\!-\!\!\left\langle\!\!\!\begin{array}{c}\phantom{x}\end{array}\!\!\!\right\rangle\!\!-O-CH_2-CHOH-CH_2X \quad (6)$$

and $$X-CH_2-CHOH-CH_2-S-(CH_2)_q-S-CH_2-CHOH-CH_2X, \quad \text{wherein} \quad (7)$$

q = 2–6, and X in (1)–(7) above represents Cl or Br;
a bis-azetidinium of the formula $$HO-\!\!\left\langle\!\!\!\begin{array}{c}\phantom{x}\\N\\\oplus\end{array}\!\!\!\right\rangle\!\!\diagdown\!\!\diagup N-CH_2-CHOH-CH_2-N\diagdown\!\!\diagup\!\!\left\langle\!\!\!\begin{array}{c}\phantom{x}\\N\\\oplus\end{array}\!\!\!\right\rangle\!\!-OH; \quad (8)$$
$$\phantom{HO-}Cl^\ominus\phantom{xxxxxxxxxxxxxxxxxxxxxxxxxxxx}Cl^\ominus$$

a bis-haloacyl diamine of the formula $$X-(CH_2)_n-CON-A-NCO-(CH_2)_nX, \quad \text{wherein } X = \text{Cl or Br,} \quad (9)$$
$$\phantom{X-(CH_2)_n-}|\phantom{CON-A-N}|$$
$$\phantom{X-(CH_2)_n-}R_1\phantom{CON-A-N}R_2$$

$$A = -CH_2-CH_2-, \ -CH_2-CH_2-CH_2- \ \text{or} \ -\overset{\overset{O}{\|}}{C}-, \ n = 1\text{-}10, \ R_1 = R_2 =$$

hydrogen or $R_1$ and $R_2$ linked together represent ethylene; when

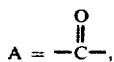

$R_1$ and $R_2$ represent hydrogen, when $A=-CH_2-CH_2-$, $R_1$ and $R_2$ can be linked together and represent ethylene with the group 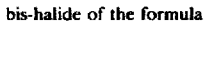 representing

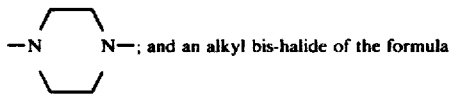; and an alkyl bis-halide of the formula

-continued

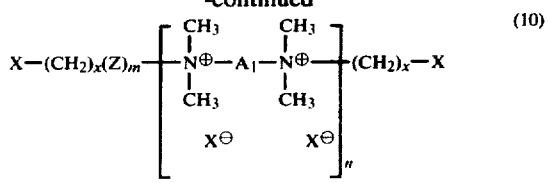 (10)

wherein $X = Cl$ or $Br$, $Z$ represents 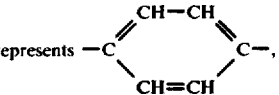, $x=1-3$, $m=0$ or $1$, $n=0$ or $1$, $m$ and $n$ not representing $1$ at the same time, when $m=1$, $x=1$; and $A_1$ represents a divalent hydrocarbon radical having $2$, $3$, $4$ or $6$ carbon atoms or 2-hydroxy propylene.

16. The cosmetic composition of claim 1 wherein said crosslinking agent is selected from the group consisting of

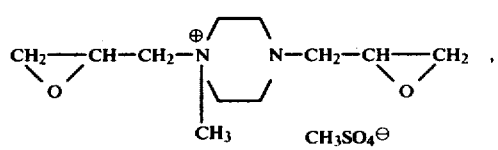 (1)

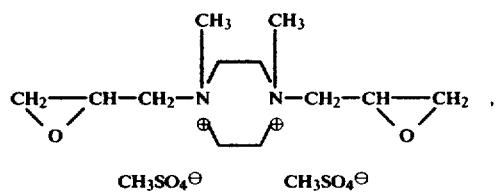 (2)

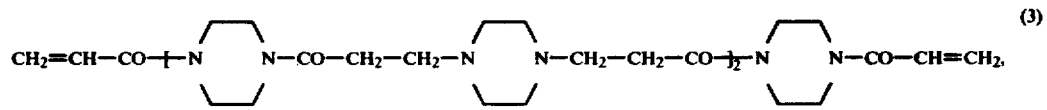 (3)

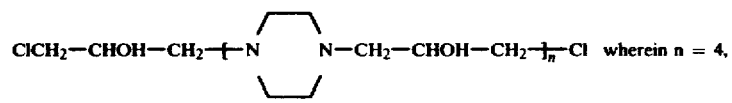 wherein $n = 4$, (4)

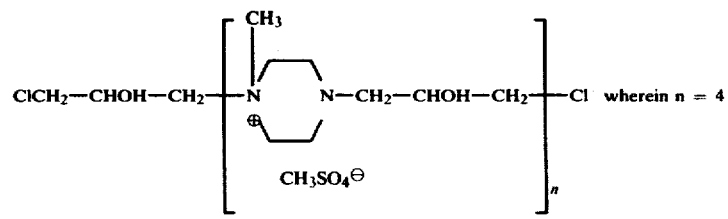 wherein $n = 4$ (5)

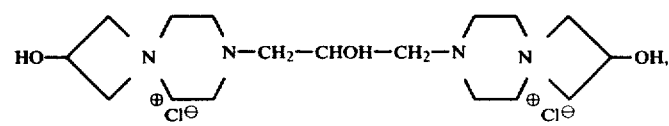 (6)

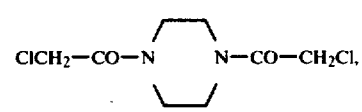 (7)

-continued

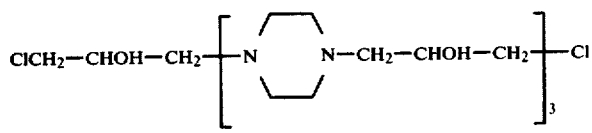
(8)

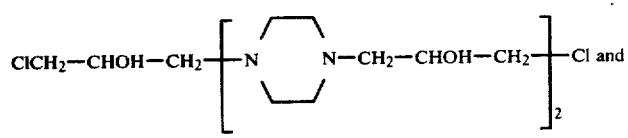
(9)

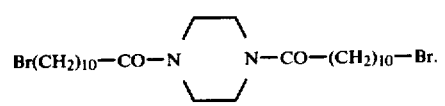
(10)

17. The cosmetic composition of claim 1 which also includes a non-ionic, anionic, cationic, amphoteric or zwitterionic surfactant to provide a shampoo composition.

18. The cosmetic composition of claim 1 which also includes a hair restructuring agent.

19. The cosmetic composition of claim 1 having a pH between 2 and 11.

20. The cosmetic composition of claim 1 having a pH betwen 3 and 8.

21. The cosmetic composition of claim 1 which also includes a water-soluble electrolyte.

22. The cosmetic composition of claim 21 wherein said water-soluble electrolyte is sodium chloride, sodium acetate, potassium chloride, potassium acetate, ammonium chloride, ammonium acetate, calcium chloride or calcium acetate.

23. The cosmetic composition of claim 21 wherein said water-soluble electrolyte is present in an amount of 0.01–5 percent by weight of said composition.

24. The cosmetic composition of claim 1 which also includes a cosmetic film-forming resin.

* * * * *